US011944318B2

(12) United States Patent
Whelan

(10) Patent No.: US 11,944,318 B2
(45) Date of Patent: Apr. 2, 2024

(54) SURGICAL CLAMP

(71) Applicant: VASCULAR DEVICES PTY LTD., Victoria (AU)

(72) Inventor: Geoffrey Paul Whelan, Victoria (AU)

(73) Assignee: VASCULAR DEVICES PTY LTD., Balwyn North (AU)

( * ) Notice: Subject to any disclaimer, the term of this patent is extended or adjusted under 35 U.S.C. 154(b) by 181 days.

(21) Appl. No.: 16/632,234

(22) PCT Filed: Jul. 18, 2018

(86) PCT No.: PCT/AU2018/000117
§ 371 (c)(1),
(2) Date: Jan. 17, 2020

(87) PCT Pub. No.: WO2019/014699
PCT Pub. Date: Jan. 24, 2019

(65) Prior Publication Data
US 2020/0170643 A1 Jun. 4, 2020

(30) Foreign Application Priority Data

Jul. 18, 2017 (AU) ................................ 2017902816
Jul. 18, 2017 (AU) ................................ 2017902817
May 10, 2018 (AU) ................................ 2018901600

(51) Int. Cl.
*A61B 17/122* (2006.01)
*A61B 17/00* (2006.01)
A61B 90/92 (2016.01)

(52) U.S. Cl.
CPC .. *A61B 17/122* (2013.01); *A61B 2017/00407* (2013.01); *A61B 2017/00526* (2013.01); *A61B 90/92* (2016.02)

(58) Field of Classification Search
CPC .......... A61B 2017/00407; A61B 17/12; A61B 2017/00526; B25B 5/068
See application file for complete search history.

(56) References Cited

U.S. PATENT DOCUMENTS 3,510,923 A 5/1970 Blake
4,120,302 A 10/1978 Ziegler
(Continued)

FOREIGN PATENT DOCUMENTS

EP 1562492 A1 8/2005
EP 1878390 A1 1/2008
(Continued)

OTHER PUBLICATIONS

Applicant: Vascular Devices Pty Ltd; "Surgical Clamp"; European Patent Application No. 18835132; Mar. 16, 2021; 14 pgs.

*Primary Examiner* — Sarah A Long
*Assistant Examiner* — Raihan R Khandker
(74) *Attorney, Agent, or Firm* — TAROLLI, SUNDHEIM, COVELL & TUMMINO L.L.P.

(57) ABSTRACT

A surgical clamp is disclosed. The surgical clamp comprises a two-piece body comprising atop jaw housing that inter-fits with a bottom jaw housing; the top jaw housing comprising a top jaw; the bottom jaw housing comprising a bottom jaw; the inter-fitting top jaw housing and bottom jaw housing disposed for movement relative to one another; a bias to the top jaw housing and bottom jaw housing apart; and a lever moveable between a lock position and an open position and the lever disposed to prevent opening movement of the top jaw housing relative to the bottom jaw housing and to allow graduated relative closing movement of the top jaw housing relative to the bottom jaw housing in the lock position and to allow opening and closing movement of the top jaw housing relative to the bottom jaw housing in the open position. The structure of the clamp is such that compressive (Continued)

force applied to one or more of the top jaw housing and the bottom jaw housing causes graduated closing movement of the top jaw housing and the bottom jaw housing to close the top jaw and the bottom jaw. The lever may comprise an axial arm and a lateral arm wherein the axial arm comprises one or more tooth or pawl disposed at a distal end of the axial arm and the lateral arm comprises a button disposed on a distal end of the lateral arm wherein pressing the button or the distal end pivots or moves the axial arm. The pivoting or movement may be oblique pivoting or movement and may disengage the one or more tooth from the rack.

14 Claims, 17 Drawing Sheets

(56) References Cited

U.S. PATENT DOCUMENTS

| | | | |
|---|---|---|---|
| 4,800,879 A | 1/1989 | Golyakhovsky | |
| 5,624,454 A * | 4/1997 | Palti | A61B 17/282 606/151 |
| 5,697,942 A | 12/1997 | Palti | |
| 5,921,996 A | 7/1999 | Sherman | |
| 6,036,706 A | 3/2000 | Morejohn | |
| 6,126,671 A | 10/2000 | Richards et al. | |
| 6,461,363 B1 | 10/2002 | Gadberry et al. | |
| 6,582,451 B1 | 6/2003 | Marucci | |
| 6,656,205 B1 | 12/2003 | Manhes | |
| 2005/0113634 A1 | 5/2005 | Burbank | |
| 2005/0113852 A1 | 5/2005 | Burbank | |
| 2005/0222590 A1 * | 10/2005 | Gadberry | A61B 17/1227 606/151 |
| 2007/0112365 A1 | 5/2007 | Hilal et al. | |
| 2013/0138127 A1 | 5/2013 | Buckman et al. | |
| 2015/0257776 A1 | 9/2015 | Sauer | |
| 2016/0051254 A1 | 2/2016 | Allred | |
| 2016/0249931 A1 | 9/2016 | Roig et al. | |
| 2017/0157748 A1 * | 6/2017 | Wang | B25B 13/12 |

FOREIGN PATENT DOCUMENTS

| | | |
|---|---|---|
| EP | 2987455 A1 | 2/2016 |
| GB | 2124502 A | 2/1984 |
| WO | 2009048367 A1 | 4/2009 |

* cited by examiner

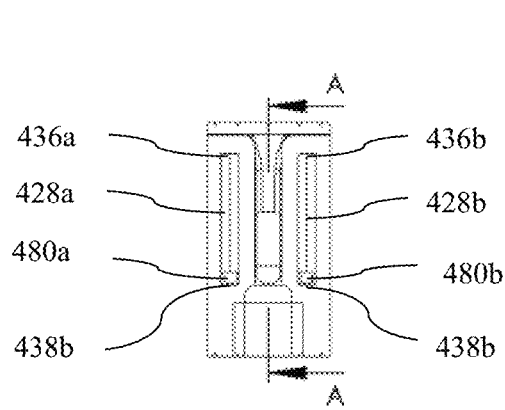
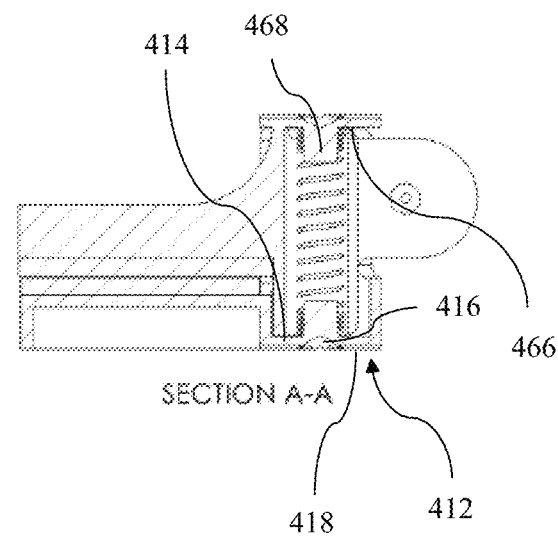
FIG. 4E
FIG. 4F
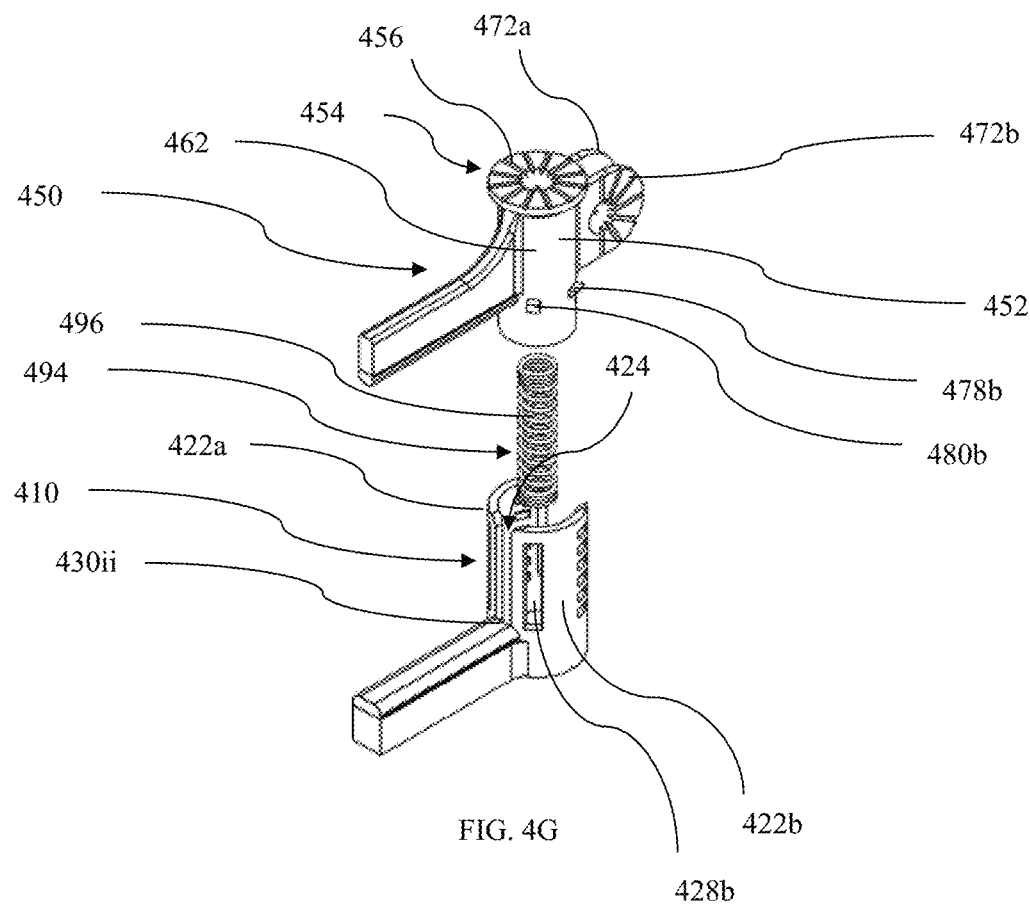
FIG. 4G

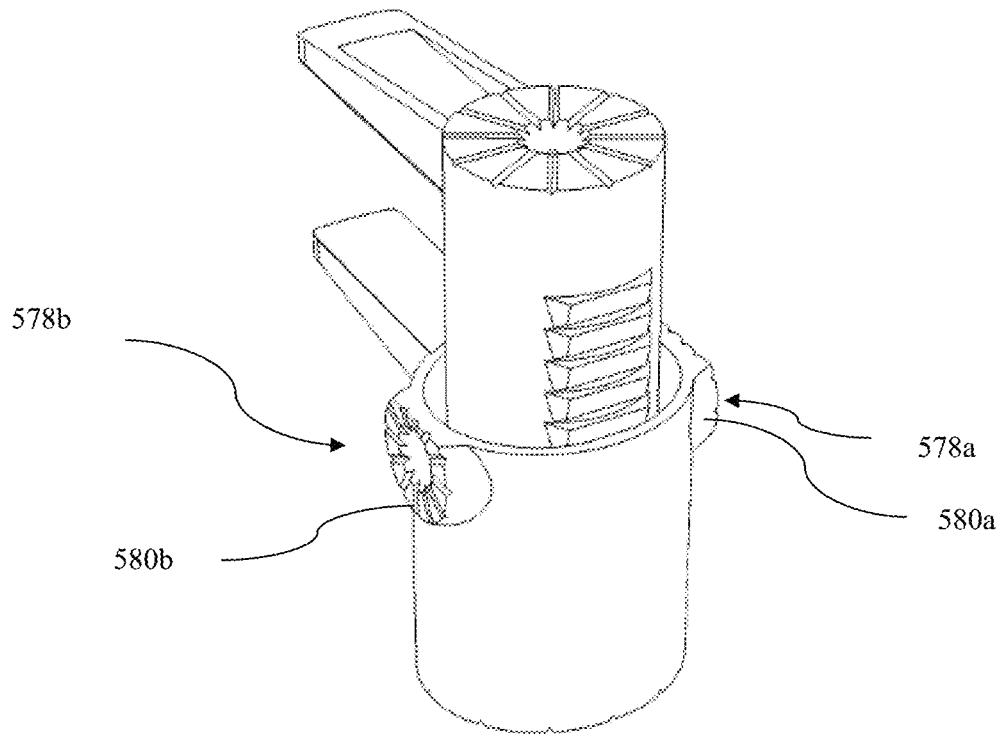
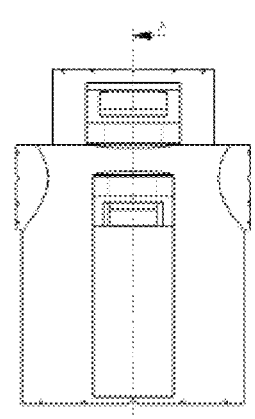
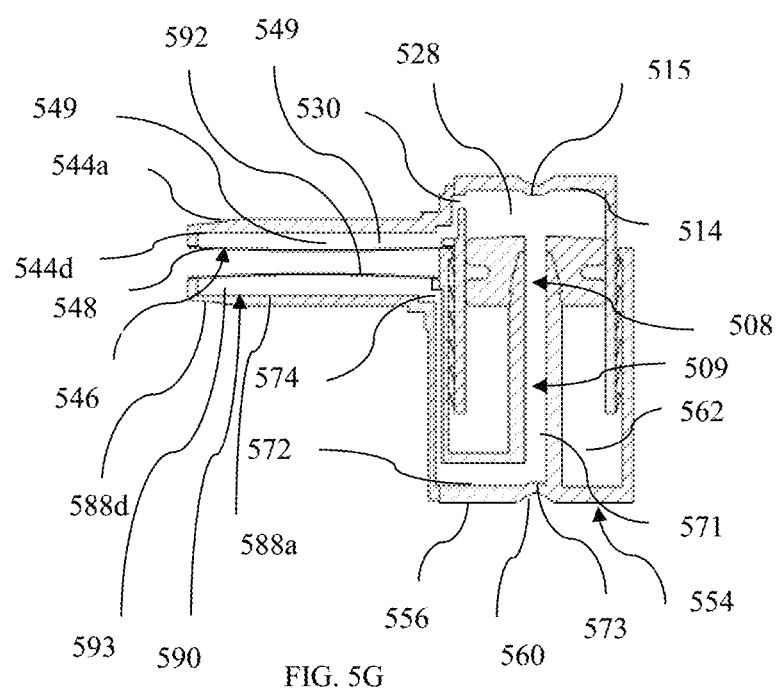
FIG. 5E
FIG. 5F
FIG. 5G

SURGICAL CLAMP

FIELD OF THE INVENTION

The present invention relates to a surgical clamp. In particular, but not exclusively, the present invention relates to a surgical clamp comprising an actuator which may be moved to release the clamp.

BACKGROUND TO THE INVENTION

During many surgical procedures it is necessary to temporarily constrict or occlude the blood flow in blood vessels, such as veins and arteries. This is typically achieved with a surgical clamp comprising a pair of elongate clamping members. A clamping member is positioned either side of the vein or artery, or either side of body tissue comprising the vein or artery, and the clamping members are biased towards each other to hold the vein, artery or body tissue therebetween. Biasing is typically achieved via a spring, a ratchet mechanism or by hand depending on the type of clamping device and the location of the vein, artery or body tissue being clamped.

Blood vessel clamps, for example, are available from manufacturers in a range of sizes suited to clamping blood vessels ranging from very small to about 2 cm. Some clamps have a pre-set clamping tension for each respective clamp size, while other larger clamps are manually operated using a ratcheting closure system requiring the operator to estimate the appropriate level of force required to occlude blood flow in the blood vessel. Smaller clamps comprise shorter clamping members and smaller springs, which exert a lower clamping force in an effort to avoid damage to the respective blood vessels. Conversely, larger clamps comprise longer clamping members and stronger springs, which exert a higher clamping force to constrict or occlude blood flow in larger blood vessels. Such clamps can be single clamps or a pair of clamps mounted to a rod or pin and spaced apart for clamping two different locations of a single blood vessel.

For some types of surgery, the pair of elongate clamping members is provided at the end of a pair of elongate handles, such as with forceps, such that clamping within a body cavity can be achieved more easily. In this example, the clamping members are typically retained in one of a plurality of predetermined separation positions via a releasable ratchet mechanism.

One disadvantage of the aforementioned prior art clamping devices is that the force exerted on the vein, artery or tissue by the clamping members can vary quite significantly. The ratchet or scissor-type clamps can exert a very high force because of the mechanical advantage the user has when operating them. This will depend on the size and type of clamp used, the size and type of spring or other biasing means employed, the type of vein or artery being clamped and the amount and type of tissue surrounding the vein or artery. For example, muscle has a high tensile strength whereas fat has a low tensile strength. If the force is too low, the desired level of blood flow constriction or occluded blood flow will not be achieved and if the force is too high, the vein or artery could be damaged leading to potentially life-threatening complications. Examples of such complications include thrombosis, which is a result of damage to the blood vessel at the point of clamping, and heart attacks or strokes caused by dislodgement of plaque material at the clamping site.

Often the pressure exerted by the clamping members is non-uniform along their length resulting in a pressure gradient. Many clamps apply inconsistent pressure which causes damage to the blood vessel from uneven pressure being applied to the blood vessel.

Another drawback of conventional surgical clamps and, in particular, manually operated clamps that are available in a range of sizes and shapes, is the cost. For example, a batch of 10 surgical clamps of a single size and shape can cost about $500. A single size of clamp may only be suitable for a specific type of surgery and such clamps are often disposable, single-use clamps. Therefore, medical facilities experience significant expenditure in providing and maintaining sufficient numbers of clamps in the required range of sizes. Furthermore, a particular size of clamp may be suitable for exerting an appropriate level of force on a particular blood vessel in one patient, but this may be excessive or insufficient for the same blood vessel in the same procedure in a different patient, for example, due to varying levels of plaque build-up between patients.

Metal surgical clamping devices can be sterilized and reused, which addresses to an extent the cost associated with replacing single use clamping devices. However, reusable metal surgical clamping devices usually have a greater initial cost. Also, at least some of the metal surgical clamping devices experience metal fatigue after repeated use, which can lead to cracks in the metal that can cause infection. Metal surgical clamps also tend to lose clamping tension due to repeated use.

Various attempts have been made to alleviate at least some of these problems. For example, European Patent No.: 1562492 discloses an apparatus for the detection and occlusion of blood flow comprising a pair of elongate clamping members for clamping tissue comprising an artery. The apparatus is similar to a pair of forceps and comprises a releasable ratcheting mechanism to maintain pressure between the clamping members. One of the clamping members comprises a blood flow detecting sensor to facilitate the location or monitoring of the artery to be occluded. The sensor can detect the reduction or abolition of blood flow and the releasable ratcheting mechanism can be adjusted to change the blood flow.

The apparatus of European Patent No.: 1562492 is particularly suited for occluding blood flow in uterine arteries. However, blood flow is still dependent on and controlled by the manual adjustment of the releasable ratcheting mechanism by the nurse or surgeon, thus still requiring the necessary skill and care in applying the correct pressure for the particular procedure, the particular region of the body and the particular patient. Furthermore, the blood flow detecting sensor is coupled to a sensor control device via a detachable cable external to the elongate arms of the device. The external cable can potentially interfere with the procedure and can present a snagging risk in relation to other apparatus or protruding elements in the operating theatre. Therefore, the external cable is considered to be undesirable. Whilst the elongate arms facilitate access to body cavities, the elongate arms render the clamping apparatus disclosed in European Patent No.: 1562492 unusable for many procedures where clamping in confined cavities is required.

Other clamping or occlusion devices are known such as, those discussed briefly below. However, at least some of the clamping or occlusion devices in these documents exhibit one or more of the aforementioned problems.

United States of America Patent Publication No.: 2005/0113634 teaches an occluding device that has a pair of pivotally connected occluding members, with at least one occluding member having a movable occluding element on a distal shaft section. The position and orientation of the occluding elements on the distal shaft sections may be adjusted by operative members on the proximal shaft sections of the occluding members to accommodate for asymmetrical uterine artery anatomy. The occluding elements have pressure applying surfaces with one or more blood flow sensors such as Doppler chips which help the physician to better identify the uterine artery and to monitor blood flow therein.

United States Patent Publication No.: 2005/0113852 describes an intravaginal uterine artery occlusion device that has a cervical receptacle or cap with an open distal end for receiving the patient's uterine cervix and an elongated shaft having a distal end secured to the closed proximal end of the cervical receptacle and an inner lumen extending to the distal end of the elongated shaft. The patient's uterine cervix is held within the interior of the receptacle by the application of a vacuum to the interior of the receptacle through the inner lumen of the shaft or otherwise, while the leading edge(s) of the cervical receptacle presses against the patient's vaginal fornix to occlude an underlying or adjacent uterine artery. A blood flow sensor is taught to be provided on the leading edge of the receptacle to aid in locating a uterine artery and to monitor blood flow through the located uterine artery.

International Patent Publication No.: WO2009/048367 discloses an electronic controller housed within a body that is coupled to control movement of at least one clamping member to control a pressure exerted by the clamping members on a blood vessel clamped therebetween. At least one blood flow sensor is mounted to at least one of the clamping members to detect blood flow in the blood vessel so that the clamping members can be locked in place when blood flow has been occluded or constricted to the desired extent.

U.S. Pat. No. 6,582,451 discloses an instrument to manipulate the tissue of a body of a patient that has jaws that move away from each other in a parallel motion. The articulating means for the jaws comprises a scissor type linkage and movement of the jaws is enacted through the reciprocating rod acting upon one end of said scissors linkage.

U.S. Pat. No. 6,656,205 is directed to an instrument for application in endoscopic surgery that has a shaft provided with a plurality of ducts, two of which receive forceps elements and one of which receives a surgical instrument for cooperation with the forceps elements. One of the forceps elements has a distal end pivotal about a pivot axis which extends orthogonally to a longitudinal axis of the shaft, so that the distal ends of the forceps elements can be displaceable at a distance greater than an outer dimension of the shaft upon its insertion into a corporeal cavity.

European Patent No.: 1878390 provides a sternum retractor device suitable for temporarily maintaining a gap between the two sternal stumps in cardiosurgical procedures. The retractor device has a pair of jaws configured to be inserted between the two sternal stumps and shaped to engage firmly on the stumps, actuating means connected to the jaws for controlling their closing and opening movements and means for the controlled feed or withdrawal of a biocompatible actuator fluid in/from the actuating means. The actuating means take effect in a direction substantially perpendicular to the direction of the divarication of said stumps and are connected to the jaws by means of an articulated mechanism that moves the jaws closer together or further away from one another.

U.S. Pat. No. 4,800,879 teaches a disposable vascular occluding device constructed with two plastic arms connected at one end by a hinge for pivoting the arms towards and away from each other and connected at an end opposite the hinged end by a toothed latch for releasably securing the plastic arms in a closed position with inner surfaces thereof confronting each other. The inner surfaces of the plastic arms are lined by a pair of partially-inflated soft plastic balloons, centered in the cavities, one of which is further inflatable by means of an ordinary syringe through a valve in one of the plastic arms. The device facilitates occlusion of a blood vessel with minimal or no traumatization of the wall of the blood vessel.

U.S. Pat. No. 5,921,996 is directed to a surgical clamp applier and a detachable clamp for temporarily occluding a vessel. The elongate clamp applier is designed to allow a surgeon to distally place and remove the clamp using only one hand. The clamp applier has a dial, a button, and a pulley actuator all accessible on the handle of the applier. The dial is used to lock the clamp onto the applier and to remove the clamp from the applier. The button is used to allow the pulley actuator to be used to manipulate the lower jaw of the clamp with respect to the upper jaw of the clamp, thus varying the amount of pressure exerted by the clamp on the vessel. The pulley actuator actuates a pulley system which engages the clamp, thereby manipulating the lower jaw of the clamp with respect to the upper jaw in a scissors-like manner, allowing the surgeon to properly clamp the target vessel.

U.S. Pat. No. 4,120,302 teaches a disposable pad including a flexible elongated member having a channel therein for slidably receiving a supporting element. A stop member limits longitudinal insertion of the supporting element into the channel, a retention member prevents lateral movement of the supporting element out of the channel, and a latching member secures the supporting element against longitudinal displacement from the channel. The latching member is normally disposed in a latching position but is shiftable into a releasing position as the elongated member is flexed to remove the pad. The supporting element of the surgical instrument can hold an artery or vein or other body tissue without damage when using the disposable pad.

U.S. Pat. No. 5,697,942 is directed to a vascular clamp that has a pair of clamping jaws movable between a first, open position and a second, closed position, and means integral with and securing the clamping jaws to one another for movement from their open to their closed position, the securing means together with the clamping jaws defining a substantially closed internal chamber having substantially continuous internal walls when the clamping jaws are in their closed position. A balloon is mounted to the internal walls of each clamping jaw and pre-filled with a fluid under a predetermined pressure such that the balloons may completely surround and occlude the blood vessel or duct when the clamping jaws are in their closed position.

U.S. Pat. No. 6,036,706 describes a vascular clamp assembly that has a pair of clamping members located at a distal part of a bendable elongated shaft. Balloons that can be inflated with air, water or saline are located on the clamping members.

U.S. Pat. No. 3,510,923 to Lawrence W. Blake discloses a pair of opposed jaws molded integrally with the upper ends of two telescoping members which form a barrel and a plunger. The back side of the barrel is equipped with downwardly sloping ratchet teeth and a pinch grip is integral with the upper end of the barrel. The pinch grip slidably receives the spring arm of a second pinch grip. The spring arm is integral with one of the jaws and the plunger and is equipped with a pawl to engage ratchet teeth on the barrel.

U.S. Pat. No. 3,509,882 also to Lawrence W. Blake is directed to a jaw spring clamp which also has opposed jaws molded integrally with the upper ends of two telescoping members which form a barrel and a plunger. A metal compression spring is contained with the plunger and barrel to urge the jaws towards a closed position. The jaws can be separated by pinching the top and bottom of the clamp.

United States Patent Publication 2007/0112365 teaches a clip with two jaws attached at their ends to symmetrical connectors which have pivot points to allow the jaws to open and increase the span between the jaws. One of the connectors has teeth which govern or provide incremental closing of the jaws.

U.S. Pat. No. 6,126,671 discloses a clamp that has a pair of grasping elements disposed on clamp arm members. The clamp includes a spring disposed within a handle member. When force is applied to one end, a plunger slides further into the handle member. When the plunger is fully depressed into the handle member, the clamp is in its open position. When pressure is released from the same end, the internal spring acts on the plunger to place the clamp in a closed position.

U.S. Pat. No. 4,976,721 teaches an intestinal occluding clamp that has a housing, a base, a cap and a spring biasing means. The housing has a housing cavity and a first jaw is connected to and projects away from the housing cavity. A bottom wall of the housing cavity has an aperture formed therethrough. The base has a second jaw and a base post which projects from the body of the base. The cap has a stem which projects downwardly. The spring is disposed with the housing cavity about the base post. The cap stem is inserted through the bore in the base post. The cap is retractably insertable into the housing cavity by pressing down on the cap. To maintain the clamp in the open locked position the housing includes a lock tab and the base post includes a lock flange. The lock tab and lock flange lockingly inter-engage when the cap is pushed fully down into the housing cavity and the bottom edge of the cap side walls contact the fulcrum means and the cap pivots forwards rotating the lock flange under the lock tab. To release the jaws the rear side of the cap is depressed.

U.S. Pat. No. 6,267,773 is directed to a surgical spring clip that has a telescoping barrel formed with an outer barrel portion moveable along an axis relative to an inner barrel portion. Extending on one side of the barrel are a pair of jaws. On the opposite of the barrel are a pair of supports or tabs. The clip is operable by movement of the tabs between a closed position and an open option. In the open position, the tabs are moved into proximity against a bias of the spring to separate the jaws. As the tabs are forced into proximity, the telescoping barrel tends to function as a fulcrum, causing the tops of the jaws to tilt toward each other. To inhibit the tilting, a pair of projections are provided to tilt the entire inner barrel position backwardly within the cavity.

International Patent Publication No.: WO 01/58367 discloses four types of surgical occlusion devices. The first type has jaws pivotally coupled by a rivet and closing force provided by a compression spring. The second type has jaws that are opened by pressing two components of a telescoping barrel together to compress a spring. The third type differs from the second by having grips extend from the telescoping barrel. The fourth type uses a single piece construction with a hairpin turn and crossover to provide the bias.

International Patent Publication No.: WO 96/11635 describes a vessel clip that has jaws and telescoping cylinders moving against the bias of a spring.

The reference to any prior art in this specification is not, and should not be taken as, an acknowledgement or any form of suggestion that the prior art forms part of the common general knowledge.

SUMMARY OF THE INVENTION

Generally, embodiments of the invention relate to a surgical clamp. In a particular embodiment, the invention relates to a surgical clamp comprising an actuator which may be moved to release the clamp. The actuator may comprise a lever which may be moved obliquely to release the clamp.

In a first form, although it need not be the only or indeed the broadest form, the invention resides in a surgical clamp comprising:
   a two-piece body comprising a top jaw housing that inter-fits with a bottom jaw housing;
   the top jaw housing comprising a top jaw;
   the bottom jaw housing comprising a bottom jaw;
   the inter-fitting top jaw housing and bottom jaw housing disposed for movement relative to one another;
   a bias to the top jaw housing and bottom jaw housing apart;
   a lever moveable between a lock position and an open position and the lever disposed to prevent opening movement of the top jaw housing relative to the bottom jaw housing and to allow graduated relative closing movement of the top jaw housing relative to the bottom jaw housing in the lock position and to allow opening and closing movement of the top jaw housing relative to the bottom jaw housing in the open position;
   such that compressive force applied to one or more of the top jaw housing and the bottom jaw housing causes graduated closing movement of the top jaw housing and the bottom jaw housing to close the top jaw and the bottom jaw.

In a second form, the invention provides a method of clamping a blood vessel, tissue or other body part with the clamp of the first form.

In a third form, the invention provides a method of manufacturing a clamp of the first form.

In a fourth form, the invention provides a method of manufacturing a surgical clamp comprising:
   assembling a two-piece body comprising a top jaw housing that inter-fits with a bottom jaw housing, a bias to the top jaw housing and bottom jaw housing apart and a lever, the lever moveable between a lock position and an open position and the lever disposed to prevent opening movement of the top jaw housing relative to the bottom jaw housing and to allow graduated relative closing movement of the top jaw housing relative to the bottom jaw housing in the lock position and to allow opening and closing movement of the top jaw housing relative to the bottom jaw housing in the open position;
   the top jaw housing comprising a top jaw;
   the bottom jaw housing comprising a bottom jaw;
   the inter-fitting top jaw housing and bottom jaw housing disposed for movement relative to one another;
   such that compressive force applied to one or more of the top jaw housing and the bottom jaw housing causes graduated closing movement of the top jaw housing and the bottom jaw housing to close the top jaw and the bottom jaw.

In one embodiment of the fourth form, the surgical clamp manufactured is the surgical clamp of the first form.

In one embodiment of any one of the above forms, the lever comprises an axial arm and a lateral arm wherein the axial arm comprises one or more tooth or pawl disposed at a distal end of the axial arm and the lateral arm comprises a button disposed on a distal end of the lateral arm wherein pressing the button or the distal end pivots or moves the axial arm. The pivoting or movement may be oblique pivoting or movement and may disengage the one or more tooth from the rack.

In one embodiment of any one of the above forms, the lever comprises a component part of one or more of a ratchet, a rack and pinion, or a damper or another mechanical device permitting graduated movement. The ratchet, rack and pinion, or damper or other mechanical device may permit two-way movement to open and close the pair of jaws. In one particular embodiment of the first form, the lever comprises a component part of a ratchet. The lever may comprise one or more pawl or tooth of the ratchet. The lever may be comprised on the top jaw housing. The rack component of the ratchet may be comprised on the bottom jaw housing. The rack may comprise a plurality of teeth for inter-fitting with the lever for the graduated movement.

The rack according to any one of the above forms may comprise a linear rack. The rack may comprise a plurality of teeth. The plurality of teeth may comprise a square profile or an angled profile. The angled profile may prevent or restrict movement in one way while the one or more pawl or tooth is engaged. The one way may be opening movement. The plurality of teeth may be disposed along a length extending from a proximal end of the rack to a distal end of the rack. The proximal end may be closer to the jaw than the distal end.

According to any one of the above forms the plurality of teeth may be used to select a graduated opening position of the top jaw housing and the bottom jaw housing to open the top jaw and the bottom jaw in graduated movement. To transition to a more open position, the lever is placed in the open position, the bias is controlled and a more distal tooth on the rack is selected for engagement with the lever.

In another embodiment of any one of the above forms, the bottom jaw housing comprises a male jaw housing and the top jaw housing comprises a female jaw housing, the male jaw housing and the female jaw housing move relative to each other to move the top jaw and the bottom jaw relative to each other.

In still another embodiment of any one of the above forms, the top jaw housing comprises a male jaw housing and the bottom jaw housing comprises a female jaw housing, the female jaw housing and the male jaw housing move relative to each other to move the top jaw and the bottom jaw relative to each other.

In yet another embodiment of any one of the above forms, the top jaw housing and bottom jaw housing may comprise relative components of a ratchet and pawl, rack and pinion, damper or another mechanical device permitting graduated movement. In one embodiment, the bottom jaw housing may comprise the rack and the top jaw housing may comprise the pinion, pawl or tooth. In another embodiment, the top jaw housing may comprise the rack and the bottom jaw housing may comprise the pinion, pawl or tooth.

In yet another embodiment of any one of the above forms, the top jaw housing comprises a top base. The top base may be located on an end or a side of the top jaw housing. The top base may comprise a top exterior surface. The top exterior surface may comprise a gripping surface, grooves and/or a marking for engaging with a tool or applicator such as, forceps. The marking may comprise a cavity or a protrusion for inter-fitting with a complementary protrusion or cavity on a tool or applicator such as, the forceps.

In another embodiment of any one of the above forms, the top jaw housing comprises a top bias retaining surface. The top bias retaining surface may be comprised on any component of the top jaw housing such as, the top base and the lever.

The top jaw housing according to any one of the above forms may also comprise a top retainer. The top retainer may be raised. The top retainer may hold the bias in position. The top retainer may be comprised on any component of the top jaw housing such as, the top base and the lever. The top retainer may form part of the top bias retaining surface.

In another embodiment of any one of the above forms, the bottom jaw housing comprises a bottom base. The bottom base may be located on an end or a side of the bottom jaw housing. The bottom base may comprise a bottom exterior surface. The bottom exterior surface may comprise a gripping surface, grooves and/or a marking for engaging with a tool or applicator such as, forceps. The marking may comprise a cavity or a protrusion for inter-fitting with a complementary protrusion or cavity on a tool or applicator such as, the forceps. The bottom base may comprise a shoulder.

In another embodiment of any one of the above forms, the bottom jaw housing comprises a bottom bias retaining surface. The bottom bias retaining surface may be comprised on the bottom base.

The bottom jaw housing according to any one of the above forms may comprise a bottom retainer. The bottom retainer may be raised. The bottom retainer may hold the bias in position. The bottom retainer may be comprised on the bottom base and may form part of the bottom bias retaining surface.

In yet another embodiment of any one of the above forms, the top jaw housing comprises a top wall. The top wall may be cylindrically shaped or generally cylindrically shaped; square shaped or generally square shaped; rectangularly shaped or generally rectangularly shaped, triangularly shaped or generally triangularly shaped; ovoid or generally ovoid shaped; or of any shape. The top wall may comprise an open slot for the lever to access the rack. The top wall may comprise a top wall upper surface.

The top jaw housing may comprise a push tab. The push tab may extend out for easy gripping by a hand or finger. The push tab may also comprise one or more of a gripping surface, grooves and/or a marking for engaging with a tool or applicator such as, forceps.

In another embodiment of any one of the above forms, the bottom jaw housing comprises a bottom wall. The bottom wall may be cylindrically shaped or generally cylindrically shaped; square shaped or generally square shaped; rectangularly shaped or generally rectangularly shaped, triangularly shaped or generally triangularly shaped; ovoid or generally ovoid shaped; or of any shape. The rack may be disposed on the bottom wall. The bottom wall may comprise a bottom wall upper surface.

The top wall and/or bottom wall according to any one of the above forms may define an internal cavity or void. The top wall and/or bottom wall may be continuous or substantially continuous.

According to any one of the above forms the bottom jaw housing may comprise a push tab. The push tab may extend out for easy gripping by a hand or finger. The push tab may also comprise one or more of a gripping surface, grooves and/or a marking for engaging with a tool or applicator such as, forceps.

The top wall and bottom wall according to any one of the above forms may move along each other's length. The top wall may move inside the bottom wall. The bottom wall may move inside the top wall. The relative top and bottom wall movement may be telescopic movement. The movement of the top wall and the bottom may be delimited. The delimiting may be caused by the top wall upper surface abutting the shoulder.

According to any one of the above forms the top wall and bottom wall may comprise a complementary shape to aid the movement along each other's length. The complementary shape may comprise one or more inter-fitting ridge and slot. The one or more ridge may be comprised on the bottom wall or the top wall. The one or more slot may be comprised on the top wall or the bottom wall. The one or more ridge and slot may also prevent rotation of the top wall with respect to the bottom wall.

The lever according to any one of the above forms may comprise an axial arm and a lateral arm. The axial arm may extend from the lateral arm. The axial arm may extend in a direction between the top jaw housing and the bottom jaw housing. The lateral arm may extend in a direction of the top jaw and bottom jaw. The lateral arm and axial arm may be disposed orthogonally or at an angle to each other. The angle may be a right angle or substantially a right angle. The angle may be 80; 81; 82; 83; 84; 85; 86; 87; 88; 89; 90; 91; 92; 93; 94; 95; 96; 97; 98; 99; 100 or less than 80 or more than 100 degrees. The axial arm may comprise one or more tooth or pawl. The one or more tooth or pawl may be disposed at a distal end of the axial arm. The lateral arm may comprise a button. The button may be disposed on a distal end of the lateral arm. Pressing the button or the distal end may pivot or move the axial arm. The pivoting or movement may be oblique pivoting or movement. The pivoting or movement may disengage the one or more tooth from the rack. The button may be a region of lever of increased width to assist in applying the force required to pivot or move lever.

According to any one of the above forms, the lever may be an integral component comprising the lateral arm and axial arm and optionally the button in one piece.

The force applied by the bias according to any one of the above forms may be selectable.

According to any one of the above forms, the bias may urge the top jaw housing and bottom jaw housing apart. The bias may urge the top jaw and bottom jaw apart.

The bias according to any one of the above forms may comprise one or more of a spring and a foam. The spring may comprise a coiled spring. The foam may comprise an open-cell or closed-cell foam. The bias may comprise a pre-set clamping force. The bias may be provided with a desired amount of bias force. The coefficient of stiffness or compliance of the spring and/or foam may be selectable.

In a particular embodiment of any one of the above forms, the lever is disposed to be moved by downward or angled force applied to the body or top jaw housing. The downward or angled force applied to the body or top jaw housing may comprise the downward force applied to cause graduated closing movement of the top jaw housing and the bottom jaw housing. The downward or angled force to move the lever may be applied without moving or varying a grip used to move the top jaw housing and bottom jaw housing.

In still another embodiment of any one of the above forms, each of the pair of jaws comprise an elongate section. Each of the pair of jaws may comprise a gripping surface.

In a fifth form the invention resides in a surgical clamp comprising:

a two-piece body comprising a mechanical device and a pair of jaws;

whereby mechanical operation of the mechanical device moves the pair of jaws relative to each other in linear motion.

In one embodiment of the fifth form, the mechanical device comprises one or more of a rack and pinion, a ratchet or a damper.

In one particular embodiment of the fifth form, the mechanical device comprises a ratchet. The ratchet may permit two-way movement to open and close the pair of jaws.

In another particular embodiment of the fifth form, the mechanical device comprises a rack and pinion. The rack and pinion may comprise a rack comprised on a first piece of the two-piece body and a pinion comprised on the other piece of the two-piece body. The rack and pinion may allow two way movement.

In yet another embodiment of the fifth form, one jaw of the pair of jaws is disposed on a male housing and the other of the pair of jaws is disposed on a female housing, the male housing and the female housing move relative to each other to move the pair of jaws relative to each other. The male housing and female housing may comprise relative components of the ratchet and pawl. The male housing may comprise the rack and the female housing may comprise the pawl. The female housing may comprise the rack and the male housing may comprise the pawl. The male housing and female housing may comprise relative components of the rack and pinion. The male housing may comprise the rack and the female housing may comprise the pinion. The female housing may comprise the rack and the male housing may comprise the pinion.

In still another embodiment of the fifth form, the two-piece body comprises a rack housing and a pinion housing. In another embodiment, the two-piece body comprises a rack housing and a pawl housing.

In another embodiment of the fifth form, the rack housing comprises a base. The base may comprise a bias retaining surface and an exterior surface. The bias retaining surface may comprise a retainer. The retainer may be raised from the base. The base may be located on an end or a side of the rack housing.

In yet another embodiment of the fifth form, the rack housing base may comprise a push tab. The push tab may comprise one or more of a gripping surface, grooves and/or a marking for engaging with a tool or applicator such as, forceps.

In yet another embodiment of the fifth form, the rack housing comprises a wall. The wall may be cylindrically shaped or generally cylindrically shaped; square shaped or generally square shaped; rectangularly shaped or generally rectangularly shaped, triangularly shaped or generally triangularly shaped; ovoid or generally ovoid shaped; or of any shape. The wall may comprise opposing uprights. The opposing uprights may be separated by a jaw channel and/or an actuator channel. One or both of the opposing uprights may comprise or define a range slot.

In still another embodiment of the fifth form, the rack housing comprises a top surface. The top surface may comprise an upright top surface, a jaw channel top surface and an actuator channel top surface. Two or more of the upright top surface, jaw channel top surface and actuator channel top surface may comprise different heights.

In another embodiment of the fifth form, the upright top surface restricts movement of the two-piece body. The upright top surface may restrict movement by impeding a pawl housing and for example a base of the pawl housing.

In yet another embodiment of the fifth form, the jaw channel top surface restricts movement of the two-piece body. The jaw channel top surface may restrict movement by impeding a jaw.

In still another embodiment of the fifth form, the actuator channel top surface restricts movement of the two-piece body. The actuator channel top surface may restrict movement by impeding an actuator.

In another embodiment of the fifth form, the range slot comprises a range slot top surface and a range slot bottom surface. The range slot top surface and range slot bottom surface may restrict movement of the two-piece body. The range slot top surface and range slot bottom surface may restrict movement by impeding a locator.

In yet another embodiment of the fifth form, the rack housing comprises one or more rack. The one or more rack may comprise a rack on each side of a jaw. The racks on each side of a jaw may be equidistant from the jaw. The one or more rack may comprise a rack on each side of the rack housing. Each of the one or more rack may comprise one or more rack fenestration. The rack may comprise one, two, three, four, five, six, seven, eight, nine, ten or more than ten fenestrations.

In still another embodiment of the fifth form, the rack housing comprises one of the pair of jaws.

In another embodiment of the fifth form, the pawl housing comprises a base. The base may comprise a push tab. The push tab may comprise one or more of a gripping surface, grooves and a marking for engaging with a tool or applicator such as, forceps. The push tab may be located on an end or a side of the pawl housing.

In yet another embodiment of the fifth form, the pawl housing comprises a rod. The rod may extend from the base. The rod may comprise a rod wall. The rod wall may comprise a hollow channel. The rod wall may comprise a cutaway. The rod wall top surface and rod wall cutaway top surface may comprise different heights.

In another embodiment of the fifth form, the rod may be cylindrically shaped or generally cylindrically shaped; square shaped or generally square shaped; rectangularly shaped or generally rectangularly shaped, triangularly shaped or generally triangularly shaped; ovoid or generally ovoid shaped; or of any shape.

In still another embodiment of the fifth form, the pawl housing base comprises a bias retaining surface. The bias retaining surface may comprise a bias retainer. The bias retainer may be raised from the pawl housing base. The bias retainer may comprise a post.

In another embodiment of the fifth form, the pawl housing comprises an actuator. The actuator may comprise a handle. The handle may comprise two flanges. Each of the two flanges may comprise one or more of a gripping surface, grooves and a marking for engaging with a tool or applicator such as, forceps. The actuator may provide graduated movement and/or clamping force. The actuator may be located on an end or a side of the pawl housing. The actuator may be located adjacent a cutaway.

In yet another embodiment of the fifth form, the pawl housing comprises one or more pawl. The one or more pawl may be comprised on the rod. Each of the one or more pawl may be comprised on the rod wall. Each of the one or more pawl may be dimensioned to fit within each of the rack fenestrations.

In still another embodiment of the fifth form, the pawl housing comprises one or more locator. Each of the one or more locator may comprise a protuberance dimensioned to fit within a range slot. The one or more locator may comprise a locator on each side of a jaw.

In another embodiment of the fifth form, the pawl housing comprises one of the pair of jaws.

In still another embodiment of the fifth form, each of the pair of jaws comprise an elongate section. Each of the pair of jaws may comprise a top surface, a front surface, side surfaces and a bottom surface.

In yet another embodiment of the fifth form, a pad may be disposed on a gripping surface of each pair of jaws. Each pad may comprise an elongate cushion. Each pad may comprise a hydraulic cushion, a pneumatic cushion, a gel, a foam, a rubber, a sponge, a cloth, a flexible material, a flexible material with a closed cavity pre-filled with air, fluid or gel or other cushioning to prevent or reduce trauma. The pad may comprise one or move bevel. The pad may be moulded into the jaw or may be replaceable and/or interchangeable.

Each pad may comprise a coating to prevent slippage of the blood vessel, tissue or other body part clamped.

In still another embodiment of the fifth form, each of the pair of jaws extend from the two-piece body.

In yet another embodiment of the fifth form, the pair of jaws comprise a rack jaw and a pawl jaw. The rack jaw may extend from the rack housing. The pawl jaw may extend from the pawl housing.

In another embodiment of the fifth form, each of the pair of jaws and/or pads are straight or concave. The concave jaws and/or pads may be sized and shaped to conform to vasculature being clamped. In a preferred embodiment, the jaws are aligned with each other.

In one embodiment of the fifth form, each of the pair of jaws may have a similar or same size. In another embodiment of the fifth form, one of the jaws is wider or longer than the other.

In a particular embodiment of the fifth form, the two-piece body and/or the actuator is/are proximal, adjacent and/or adjoins the pair of jaws. The adjoining may be without an elongate spacing.

In another embodiment of the fifth form, each of the pair of jaws extend in parallel from the body.

In a particular embodiment of the fifth form, the two-piece body and/or the rack housing and the pawl housing is/are cylindrical. The clamp comprises a cylindrical body with two rod-shaped jaws extending therefrom.

In another embodiment of the fifth form, the clamp further comprises one or more bias. The one or more bias may comprise one or more of a spring and a foam. The spring may comprise a coil spring. The foam may comprise an open-cell or closed-cell foam. The one or more bias may comprise a pre-set clamping force. The spring may be provided with a desired amount of bias force.

In one embodiment of the fifth form, the surgical clamp is not elongate. The clamp may be unelongated, stout, squat or tubby.

In another embodiment of the fifth form, the surgical clamp is substantially or generally block shaped.

In yet another embodiment of the fifth form, the pair of jaws comprise the predominate length of the device.

In still another embodiment of the fifth form, in use the entire surgical clamp remains inside the subject.

In another embodiment of the fifth form, one or more or each exposed surface of the clamp comprise a bevel or other safety feature to minimise the likelihood of trauma.

In yet another embodiment of the fifth form, the surgical clamp is a mechanical clamp. The mechanical clamp does not comprise any electronic or electromechanical components.

In still another embodiment of the fifth form, the relative movement of the pair of jaws may comprise up and down movement or side to side movement. The relative movement may comprise one of the pair of jaws moving relative to the other or both moving.

In a sixth form, the invention provides a method of clamping a blood vessel, tissue or other body part with the clamp of the first aspect.

In a seventh form, the invention provides a method of manufacturing a clamp of the fifth aspect.

In an eighth form, the invention provides a method of manufacturing a surgical clamp comprising:
assembling a two-piece body comprising a mechanical device and a pair of jaws;
whereby mechanical operation of the mechanical device moves the pair of jaws relative to each other.

In one embodiment of the eighth aspect, the surgical clamp manufactured is the surgical clamp of the fourth aspect.

In another embodiment of any one of the above forms, each jaw further comprises a cushion and moving the pair of jaws relative to each other to open and close the pair of jaws increases or decreases fluid in one or both cushion.

In a ninth form, although it need not be the only or indeed the broadest form, the invention resides in a surgical clamp comprising:
a body comprising a mechanical device and a pair of jaws, each jaw comprising a cushion;
whereby mechanical operation of the mechanical device moves the pair of jaws relative to each other to open and close the pair of jaws and increase or decrease fluid in one or both cushion.

In one embodiment of any one of the forms herein, the fluid comprises one or more of a gas, liquid or gel. The fluid may be air and/or saline. The fluid may be a compressible or incompressible fluid.

In another embodiment of any one of the forms herein, the fluid is impelled by the mechanical device. The force associated with the impelling may be generated by opening and closing the pair of jaws.

In yet another embodiment of any one of the forms herein, the clamp further comprises one or more bias. The one or more bias may comprise one or more of a spring and a foam. The spring may comprise a coil spring. The foam may comprise an open-cell or closed-cell foam. The one or more bias may comprise a pre-set clamping force. The spring may be provided with a desired amount of bias force. Each of the one or more bias may comprise one or more of a foam or a spring. The foam may comprise an open-cell foam. The open-cell foam may be filled or partly filled with fluid. The spring may comprise a coil spring. Each of the one or more bias may comprise a pre-set force. Each of the one or more bias may be provided with a desired amount of bias force. The one or more bias may comprise a minimum force for opening. The one or more bias may comprise a rack housing bias and a pawl housing bias.

In another embodiment of any one of the forms herein, the compression of the one or more bias may result in proportionate closing of the pair of jaws. The decompression of the one or more bias may result in proportionate opening of the pair of jaws.

In yet another embodiment of any one of the forms herein, the body further comprises a fluid line. The fluid line may comprise an open system so that equal pressure is applied to both cushions. The fluid line may comprise one or more of a rack housing reservoir; a rack passage; a pawl housing reservoir; a pawl passage; a rack jaw reservoir and a pawl jaw reservoir. The fluid may be comprised in the fluid line. The fluid line may further comprise a channel. The channel may comprise one or both of a pawl channel and a rack channel.

In one embodiment of any one of the forms herein, closing the pair of jaws increases the amount of fluid and/or pressure of the fluid in the pair of jaws and the membranes and/or pads expand to contain the pressurised fluid. When the fluid is comprised in an open system, both jaws are connected to maintain the fluid pressure equally across both membranes and/or pads. Opening the pair of jaws releases the fluid pressure and contracts the membranes and/or pads.

In still another embodiment of any one of the forms herein, opening the pair of jaws decreases the amount of fluid in one or both of the rack jaw reservoir and the pawl jaw reservoir and proportionately increases the amount of fluid in one or both of the rack housing reservoir and the pawl housing reservoir. Closing the pair of jaws may increase the amount of fluid in one or both of the rack jaw reservoir and the pawl jaw reservoir and proportionately decreases the amount of fluid in one or both of the rack housing reservoir and the pawl housing reservoir. The increase and decrease in the amount of fluid in the rack jaw reservoir and the pawl jaw reservoir may inflate and/or deflate the membranes.

In another embodiment of any one of the forms herein, the proportionate increase in the amount of fluid in one or both of the rack jaw reservoir and the pawl jaw reservoir on closing of the pair of jaws and proportionate decrease in the amount of fluid in one or both of the rack jaw reservoir and the pawl jaw reservoir on opening of the pair of jaws is independent of the movement of the pair of jaws.

In a preferred embodiment of any one of the forms herein, the differential cushioning provided by increasing and decreasing the amount of fluid in the rack jaw reservoir and the pawl jaw reservoir provides greater control of the degree of force being applied to the blood vessel, tissue or other body part and a gentler and/or softer surface with improved probability of conforming to the blood vessel, tissue or other body part to thereby reduce the likelihood of trauma or damage.

In another embodiment of any one of the forms herein, the body further comprises one or more plunger. Each of the one or more plunger may comprise a stem and a cup. The cup may move up and down on the stem with the movement of the pair of jaws. The one or more plunger may comprise a rack housing plunger and/or a pawl housing plunger. The cup may engage with the one or more bias. The one or more bias may be disposed to apply its force onto the plunger. The movement of the one or more cup may compress and decompress the bias.

In still another embodiment of any one of the forms herein, each cushion comprises a membrane to retain the fluid. The membrane may comprise a soft and/or pliable material. The membrane may comprise non-porous material. The membrane may comprise material selected to reduce the likelihood of damage to blood vessel, tissue or other body part clamped. The membrane may be comprised of any suitable medical grade material such as, silicon or polymeric material.

In another embodiment of any one of the forms herein, the membranes are attached at a jaw end to a flange at a distal end of each jaw and at a housing end to the rack housing or pawl housing. In another embodiment of the first form, at a housing end, the membranes are attached to a proximal end of each jaw.

In one embodiment of any one of the forms herein, the surgical clamp comprises an actuator disposed adjacent to the pair of jaws.

In another embodiment of the ninth form, movement comprises a linear motion. The linear motion may comprise up and down motion or side to side motion.

In another embodiment of the ninth form, the mechanical device comprises one or more of a rack and pinion, a ratchet or a damper. The ratchet may permit two-way movement to open and close the pair of jaws. The rack and pinion may also permit two-way movement to open and close the pair of jaws.

In still another embodiment of the ninth form, the body may comprise a two-piece body. The two-piece body may comprise a male component and a female component.

In a particular embodiment of the ninth form, the mechanical device comprises a ratchet. The ratchet may comprise a rack comprised on a first piece of the body and a pawl comprised on another piece of the body.

In another particular embodiment of the ninth form, the mechanical device comprises a rack and pinion. The rack and pinion may comprise a rack comprised on a first piece of the body and a pinion comprised on another piece of the body.

In yet another embodiment of the ninth form, one jaw of the pair of jaws is disposed on a male housing and the other of the pair of jaws is disposed on a female housing, the male housing and the female housing move relative to each other to move the pair of jaws relative to each other. The male housing and female housing may comprise relative components of the ratchet and pawl. The male housing may comprise the rack and the female housing may comprise the pawl. The female housing may comprise the rack and the male housing may comprise the pawl. The male housing and female housing may comprise relative components of the rack and pinion. The male housing may comprise the rack and the female housing may comprise the pinion. The female housing may comprise the rack and the male housing may comprise the pinion.

In still another embodiment of the ninth form, the two-piece body comprises a rack housing and a pawl housing.

In another embodiment of an one of forms herein, the channel may allow fluid to travel within the two-piece body. The channel may comprise a rack channel and a pawl channel. The channel or a part thereof may be comprised within the plunger.

In yet another embodiment of the ninth form, the rack housing comprises a base. The base may comprise a bias retaining surface and an exterior surface. The bias retaining surface may comprise a retainer. The retainer may be raised from the base. The base may be located on an end or a side of the rack housing.

The rack housing base according to the ninth form may comprise a push tab. The push tab may comprise one or more of a gripping surface, grooves and/or a marking for engaging with a tool or applicator such as, forceps. The push tab may be located on an end or a side of the pawl housing.

In yet another embodiment of the ninth form, the rack housing comprises a rack housing wall. The rack housing wall may extend from the base. The rack housing wall may be cylindrically shaped or generally cylindrically shaped; square shaped or generally square shaped; rectangularly shaped or generally rectangularly shaped, triangularly shaped or generally triangularly shaped; ovoid or generally ovoid shaped; or of any shape.

In still another embodiment of the ninth form, the rack housing wall comprises a rim. The rim may be planar.

In yet another embodiment of the ninth form, the rack housing comprises one or more rack. The one or more rack may comprise a rack on opposing sides of the rack housing. The one or more rack may be aligned with the rack jaw. Each of the one or more rack may comprise one or more rack ridge. The rack may comprise one, two, three, four, five, six, seven, eight, nine, ten or more than ten ridges.

In still another embodiment of the ninth form, the rack housing comprises one of the pair of jaws.

In another embodiment of the ninth form, the pawl housing comprises a base. The base may comprise a push tab. The push tab may comprise one or more of a gripping surface, grooves and a marking for engaging with a tool or applicator such as, forceps. The push tab may be located on an end or a side of the pawl housing.

In yet another embodiment of the ninth form, the pawl housing comprises a pawl housing wall. The pawl housing wall may extend from the base. The pawl housing wall may be cylindrically shaped or generally cylindrically shaped; square shaped or generally square shaped; rectangularly shaped or generally rectangularly shaped, triangularly shaped or generally triangularly shaped; ovoid or generally ovoid shaped; or of any shape.

In still another embodiment of the ninth form, the pawl housing wall comprises a rim. The rim may be planar.

In still another embodiment of the ninth form, the pawl housing base comprises a bias retaining surface. The bias retaining surface may comprise a bias retainer. The bias retainer may be raised from the pawl housing base. The bias retainer may comprise a post.

In another embodiment of the ninth form, the pawl housing comprises an actuator. The actuator may comprise a handle. The handle may comprise two flanges. Each of the two flanges may comprise one or more of a gripping surface, grooves and a marking for engaging with a tool or applicator such as, forceps. The actuator may provide graduated movement and/or clamping force. The actuator may be located on an end or a side of the pawl housing.

In yet another embodiment of the ninth form, the pawl housing comprises one or more tooth. The one or more tooth may be comprised on the pawl housing wall. The one or more tooth may be comprised on an interior surface of the pinion housing wall. Each of the one or more tooth may be comprised on the pawl housing wall. Each of the one or more pawl may be dimensioned and/or positioned to inter-fit with each of the rack ridges.

In another embodiment of the ninth form, the pawl housing comprises one of the pair of jaws.

In still another embodiment of the ninth form, each of the pair of jaws comprise an elongate section. Each of the pair of jaws may comprise a top surface, a front surface, side surfaces and a bottom surface.

In yet another embodiment of the ninth form, a pad may be disposed on a gripping surface of each pair of jaws. Each pad may comprise an elongate cushion. Each pad may comprise a hydraulic cushion, a pneumatic cushion, a gel, a foam, a rubber, a sponge, a cloth or other cushioning to prevent or reduce trauma. Each pad may comprise one or more bevel.

In another embodiment of the ninth form, each pad may comprise a coating to prevent slippage of the blood vessel, tissue or other body part clamped.

In still another embodiment of the ninth form, each of the pair of jaws extend from the two-piece body.

In yet another embodiment of the ninth form, the pair of jaws comprise a rack jaw and a pawl jaw. The rack jaw may extend from the rack housing. The pawl jaw may extend from the pawl housing.

In another embodiment of the ninth form, each of the pair of jaws and/or pads are straight or concave. The concave jaws and/or pads may be sized and shaped to conform to vasculature being clamped. In a preferred embodiment, the jaws are aligned with each other.

In one embodiment of the ninth form, each of the pair of jaws may have a similar or same size. In another embodiment of the first form, one of the jaws is wider or longer than the other.

In a particular embodiment of the ninth form, the two-piece body and/or the actuator is/are proximal, adjacent and/or adjoins the pair of jaws. The adjoining may be without an elongate spacing.

In another particular embodiment of the ninth form, the two-piece body and/or the rack housing and the pawl housing is/are cylindrical. The clamp may comprise a cylindrical body with two rod-shaped jaws extending therefrom.

In a tenth form, the invention provides a method of clamping a blood vessel, tissue or other body part with the clamp of the ninth aspect.

In an eleventh form, the invention provides a method of manufacturing a clamp of the ninth aspect.

In a twelfth form, the invention provides a method of manufacturing a surgical clamp comprising:
  assembling a body comprising a mechanical device and a pair of jaws, each jaw comprising a cushion;
  whereby mechanical operation of the mechanical device moves the pair of jaws relative to each other to open and close the pair of jaws and increase or decrease fluid in one or both cushion.

In one embodiment of the twelfth aspect, the surgical clamp manufactured is the surgical clamp of the ninth aspect.

Each jaw according to any one of the forms herein may comprise one or more atraumatic material. The atraumatic material may be disposed on the gripping surface. The one or more atraumatic material may comprise an elongate cushion; a hydraulic cushion; a pneumatic cushion; a gel; a foam; a rubber; a sponge; a cloth; a flexible material; or a flexible material with a closed cavity pre-filled with air fluid or gel or other cushioning to prevent or reduce trauma. The atraumatic material may comprise one or move bevel. The atraumatic material may be moulded into the jaw or may be replaceable and/or interchangeable.

The atraumatic material, top jaw or bottom jaw according to any the forms herein may comprise a coating to prevent slippage of the blood vessel, tissue or other body part clamped.

The atraumatic material according to any of the forms herein may comprise one or more of a texture layer; a compliant layer; and a fixative layer. The texture layer may comprise an outer layer. The compliant layer may comprise a middle layer or an outer layer. When the compliant layer comprises the outer layer it may comprise a grip feature. The fixative layer may comprise an inner layer. The texture layer may comprise one or more of a mesh, a pattern and grooves. The compliant material may comprise one or more of a silicone foam, silicone overmold, extruded silicone inserts and/or springs built into the jaw. The fixative layer may comprise one or more adhesive such as, a liquid adhesive, a pressure sensitive adhesive, an overmold and/or a snap. The liquid adhesive may comprise one or more of a heat cure epoxy, a UV cure epoxy and a cyanoacrylate.

The one or more atraumatic material layer according to any one of the forms herein may comprise a die cut foam; a waterjet foam; a laser cut foam; an extruded foam. The complaint layer may comprise two or more layers. The two or more compliant layers may comprise an outer layer of a natural foam surface texture and an inner layer of silicone foam. The silicon foam may comprise a closed cell silicon foam. The compliant layer comprise a mesh The outer layer according to any one of the forms herein may comprise a natural material surface texture or may comprise texture grooves extruded therein.

The top jaw and bottom jaw according to any one of the forms herein may comprise grip features moulded directly into a gripping surface. The top jaw and bottom jaw may comprise springs. The springs may be moulded into the top jaw and bottom jaw.

The top jaw and/or bottom jaw according to any one of the forms herein may comprise a rigid cap. The rigid cap may clip onto the top jaw and bottom jaw. A compliant layer may be disposed between the rigid cap and top jaw and the bottom jaw.

The top jaw and bottom jaw according to any one of the forms herein may comprise an overmold. The overmold may comprise silicone. The silicone may be bonded through and attachment feature.

The top jaw and bottom jaw according to any one of the forms herein may comprise a pad insert. The pad insert may be inserted by sliding or snapping into place. The insert may be comprised of molded silicone or comprise an extrusion.

In still another embodiment of any one of the forms herein, each of the pair of jaws extend from the two-piece body.

In another embodiment of any one of the forms herein, each of the pair of jaws and/or atraumatic material are straight or concave. The concave jaws and/or pads may be sized and shaped to conform to vasculature being clamped. In a preferred embodiment, the jaws are aligned with each other.

In another embodiment of any one of the forms herein, each of the pair of jaws may have a similar or same size. In another embodiment of the first form, one of the jaws is wider or longer than the other.

In still another embodiment of any one of the forms herein, each of the pair of jaws extend in parallel from the body.

In yet another embodiment of any one of the forms herein, the surgical clamp is not elongate. The clamp may be unelongated, stout, squat or tubby.

In another embodiment of any one of the forms herein, the surgical clamp is substantially or generally block shaped.

In yet another embodiment of any one of the forms herein, the pair of jaws comprise the predominate length of the device.

In still another embodiment of any one of the forms herein, in use the entire surgical clamp remains inside the subject.

In another embodiment of any one of the forms herein, one or more or each exposed surface of the clamp comprise a bevel or other safety feature to minimise the likelihood of trauma.

In yet another embodiment of any one of the forms herein, the surgical clamp is a mechanical clamp. The mechanical clamp does not comprise any electronic or electromechanical components.

In still another embodiment of any one of the forms herein, the relative movement of the pair of jaws may comprise up and down movement or side to side movement. The relative movement may comprise one of the pair of jaws moving relative to the other or both moving.

In a particular embodiment of any one of the forms herein, the surgical clamp is a haemostatic clamp.

In another embodiment of any one of the forms herein, the surgical clamp is for an animal, the animal may be a mammal, the mammal may be a human. In other embodiments, the animal may be a companion animal such as, a canine or a feline, livestock such as, an equine, a bovine, an ovine, a porcine or a hircine.

In still another embodiment of any one of the forms herein, the surgical clamp may be for use in laparoscopic or keyhole surgery. When used in laparoscopic or keyhole surgery, the clamp may comprise one or more markings for engagement with a tool or applicator such as, forceps.

In yet another embodiment of any one of the forms herein, the surgical clamp may comprise a visibility or locatory feature such as a high-vis colour.

Further forms and/or features of the present invention will become apparent from the following detailed description.

BRIEF DESCRIPTION OF THE DRAWINGS

In order that the invention may be readily understood and put into practical effect, reference will now be made to embodiments of the present invention with reference to the accompanying drawings, wherein like reference numbers refer to identical elements. The drawings are provided by way of example only.

FIG. 4E is a front view of one embodiment of a surgical clamp according to the invention in a closed configuration.

FIG. 4F is a section view of through the section labelled A in FIG. 4E.

FIG. 4G is an exploded view of one embodiment of a surgical clamp according to the invention.

FIG. 5E is a rear perspective view of one embodiment of a surgical clamp according to the invention in an open configuration.

FIG. 5F is a front view of one embodiment of a surgical clamp according to the invention in an open configuration.

FIG. 5G is a section view through the section labelled A in FIG. 5F.

Figure 1A:
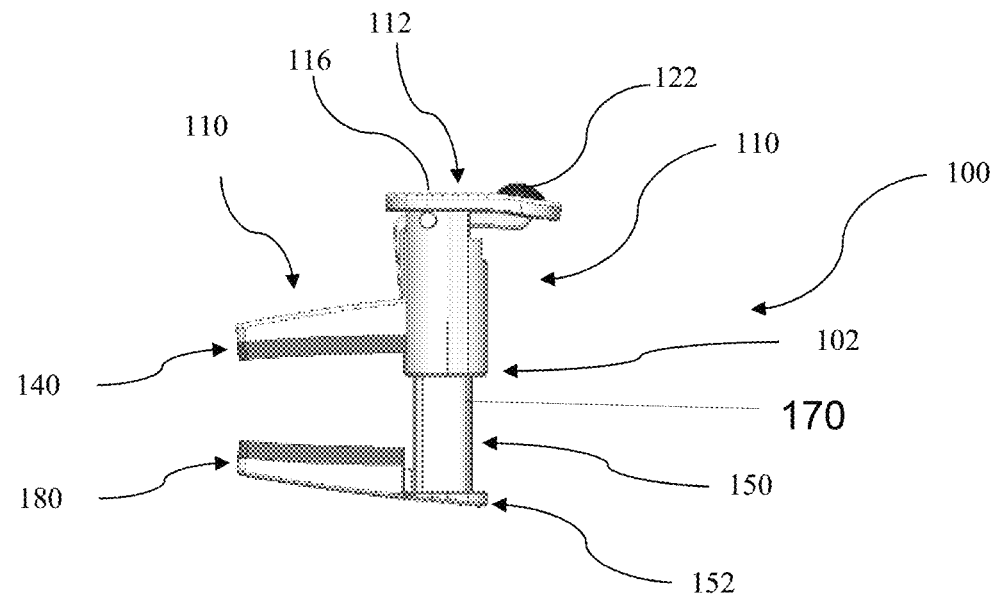
FIG. 1A is a side perspective view of one embodiment of a surgical clamp according to the invention in an open configuration.
Figure 1B:
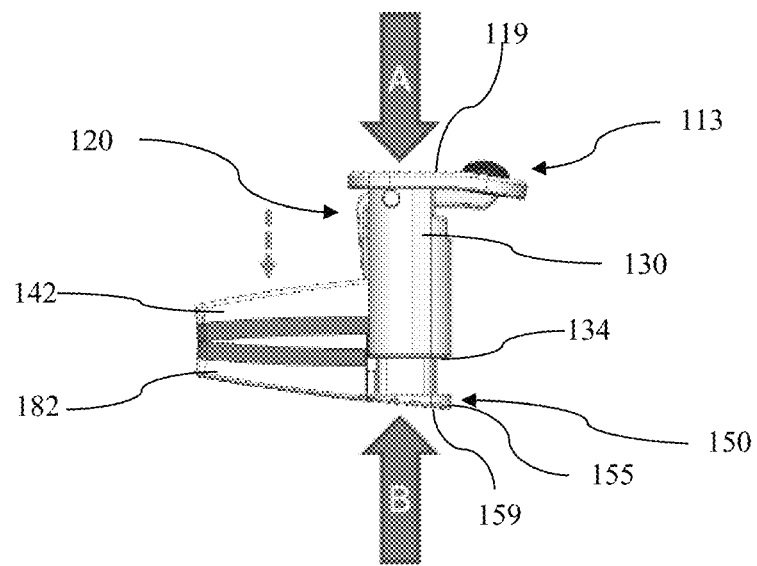
FIG. 1B is a side perspective view of the embodiment shown in FIG. 1A in a closed configuration.
Figure 1C:
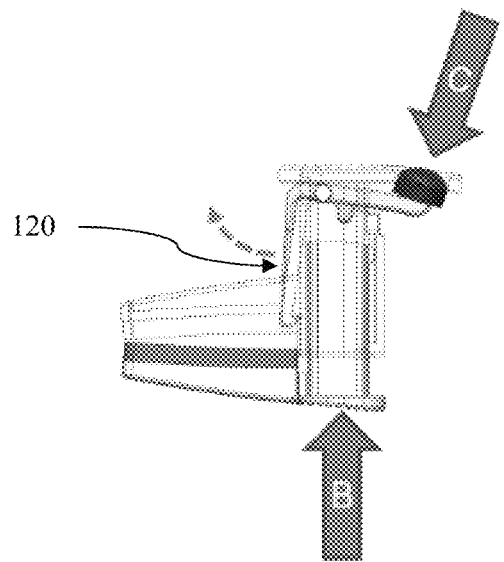
FIG. 1C is a side perspective view of the embodiment shown in FIGS. 1A and 1B in a closed configuration with partial phantom showing the lever in the open position.

Skilled addressees will appreciate that elements in the drawings are illustrated for simplicity and clarity and have not necessarily been drawn to scale. For example, the relative dimensions of some elements in the drawings may be distorted to help improve understanding of embodiments of the present invention.

DETAILED DESCRIPTION OF THE INVENTION

Embodiments of the present invention relate to a surgical clamp.

In a particular embodiment, the invention relates to a surgical clamp comprising a lever which may be moved obliquely to release the clamp.

While the invention will be described with reference to a clamp for the temporary occlusion of blood flow in a blood vessel used in various surgical procedures, it is not so limited.

Additionally, although the clamp of the invention will be described with reference to a ratchet as an example of a mechanical device for accomplishing graduated movement, the invention is not so limited and other mechanical devices can be utilised to effect movement of the two-piece body such as, a rack and pinion or a damper. Regardless of the mechanical device employed, it may permit two-way movement to open and close the pair of jaws.

FIG. 1 (FIGS. 1A; 1B; 1C; 1D; 1E; 1F; 1G; 1H; and 1I; FIG. 1A to 1I) show one embodiment of a surgical clamp 100 according to the invention. Surgical clamp 100 comprises a two-piece body 102 comprising a top jaw housing 110 that inter-fits with a bottom jaw housing 150. A top jaw 140 extends from the top jaw housing 110 and bottom jaw 180 extends from the bottom jaw housing 150.

Figure 1D:
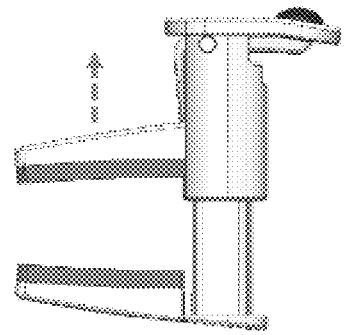
FIG. 1D is a side perspective view of the embodiment shown in FIGS. 1A, 1B and 1C in an open configuration.

The top jaw housing 110 and bottom jaw housing 150 inter-fit and are disposed for movement relative to one another. That is, top jaw housing 110 and bottom jaw housing 150 can close against one another. As shown by the arrows labelled A and B in FIG. 1B, downward force applied to housings 110, 150 closes pair of jaws 140, 180 as indicated by the dashed arrow in that same Figure. This movement can be reversed as shown in FIGS. 1D and 1G. Although only one arrow is shown in FIGS. 1D and 1G, two could be included as movement of each housing 110, 150 is possible.

Figure 1E:
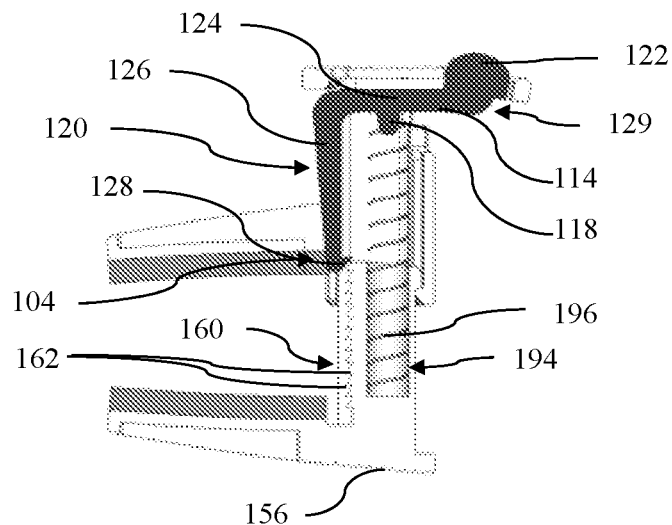
FIG. 1E is a cross-section showing a side view of the same embodiment in an open configuration with the lever in the lock position.

Shown in the cross-section provided by FIG. 1E is a bias 194, in the form of a spring 196. The bias 194 is in the direction to keep the top jaw housing 110 and bottom jaw housing 150 apart and thereby pair of jaws 140, 180 open. The direction of the bias 194 is shown in the arrow shown in FIG. 1D.

A lever 120 is shown in FIGS. 1A to 1I to be able to move between a lock position and an open position. The oblique movement or pivoting of lever 120 is indicated by the curved arrow in FIG. 1C.

Figure 1F:
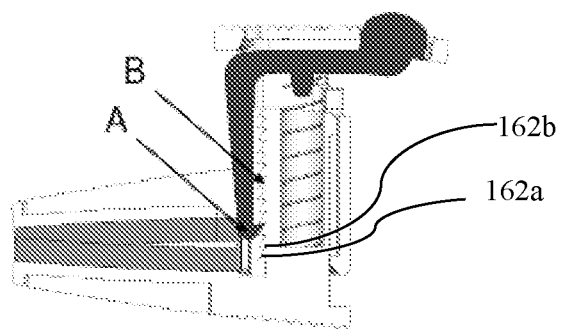
FIG. 1F a cross-section showing a side view of the same embodiment in a closed configuration with the lever in the lock position.
Figure 1G:
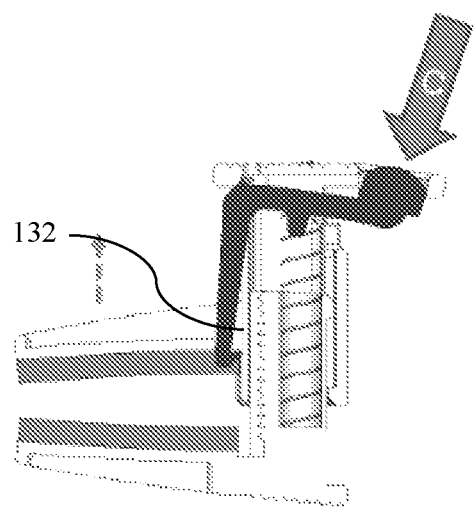
FIG. 1G is a cross-section showing a side view of the same embodiment in an open configuration with the lever in the open position.

The cross-section views shown in FIGS. 1E, 1F and 1G illustrate the actuation of lever 120. In these Figures, lever 120 is shown in solid for ease of visualisation. In the open position shown in FIG. 1G, lever 120 is disengaged from rack 160. In this open position the top jaw housing 110 and bottom jaw housing 150 can move relative to each other in either direction to open or close jaws 140, 180. The capacity to move is indicated by the dashed arrow in FIG. 1G. In the lock position, shown in FIGS. 1E and 1F, lever 120 is engaged with rack 160. In the lock position, the engagement of the tooth 128 with the rack 160 permits only one-way movement of the top jaw housing 110 and bottom jaw housing 150, graduated closing. From FIG. 1E with the jaws 140, 180, open, movement is possible for the jaws 140, 180 to move to the closed orientation shown in FIG. 1F.

When lever 120 is in the lock position, compressive force applied to one or more of the top jaw housing 110 and the bottom jaw housing 150 causes graduated closing movement of the top jaw housing 110 and the bottom jaw housing 150 to close the top jaw and 140 the bottom jaw 180.

In the embodiment shown in FIGS. 1A to 1I, lever 120 comprises a component part of a ratchet 104. In other embodiments, lever 120 may comprise a component part of a rack and pinion, or a damper or another mechanical device permitting graduated movement. By moving from the lock position to the open position, lever 120 allows two-way movement. The ratchet, rack and pinion, or damper may permit two-way graduated movement to open and close the pair of jaws 140, 180.

Lever 120 is shown to comprise one pawl or tooth 128. In other embodiments, lever 120 may comprise a plurality of pawls or teeth 128.

In the embodiment shown in FIGS. 1A to 1I, lever 120 is comprised on top jaw housing 110 and the rack 160 of ratchet 104 is comprised on the bottom jaw housing 140. In other embodiments, this positioning may be reversed with lever 120 comprised on bottom jaw housing 140 and rack 160 comprised on top jaw housing 110.

Rack 160 is shown to comprise a plurality of teeth 162 for inter-fitting with lever 120 for the graduated closing movement. In the embodiment shown, rack 160 comprises a linear rack and the plurality of teeth 162 comprise an angled profile. The angled profile may prevent or restrict movement in one way while the one or more pawl or tooth 128 is engaged. In another embodiment, the plurality of teeth may comprise a square profile. The plurality of teeth 162 are disposed along a length of rack 160 which extends from a proximal end of rack 160 to a distal end of rack 160. The proximal end is the end closer to the bottom jaw 180.

The one way movement that is prevented or restricted in the embodiment shown in FIGS. 1A to 1I, with lever 120 engaged, is opening movement. To accomplish opening movement, lever 120 is disengaged.

The plurality of teeth 162 may also be used to open jaws 140, 180 in a graduated manner. To do so, a more distal tooth 162b is selected for engagement with lever 120. To transition to a more open position, lever 120 is placed in the open position, the bias 194 is controlled and a more distal tooth 162b on rack 160 is selected for engagement with lever 120. With reference to FIG. 1F, tooth 162b is more distal than tooth 162a.

The inter-fitting of housings 110, 150 is such that bottom jaw housing 150 comprises a male jaw housing and the top jaw housing 110 comprises a female jaw housing, the male jaw housing and the female jaw housing move relative to each other to move the top jaw 140 and the bottom jaw 180 relative to each other. In other embodiments, top jaw housing 110 comprises a male jaw housing and the bottom jaw housing 150 comprises a female jaw housing, with similar movement relative to each other.

As is clear from the above, top jaw housing 110 and bottom jaw housing 150 comprise relative components of the ratchet 104 or in other embodiments the rack and pinion, damper or other mechanical device. In the embodiments shown in the Figures, the bottom jaw housing 150 comprises the rack 160 and the top jaw housing 110 comprises the pawl or tooth 128. In another embodiment, the top jaw housing 110 may comprise the rack 160 and the bottom jaw housing 150 may comprise the pawl or tooth 128.

As shown in FIG. 1A top jaw housing 110 comprises a top base 112 located on an end or a side of the top jaw housing 110. Top base 112 is also shown to comprise a top exterior surface 116 which comprises a gripping surface 119.

In the embodiment shown in FIGS. 2A to 2E the top exterior surface 116 and bottom exterior surface 156 comprise respective markings 139, 179 (bottom exterior markings 179 not shown) for engaging with a tool or applicator such as, forceps 200. As best shown in the cross-section of FIG. 2D, markings 139, 179 comprise a cavity for inter-fitting with a complementary protrusion 202 on forceps 200.

Figure 2A:
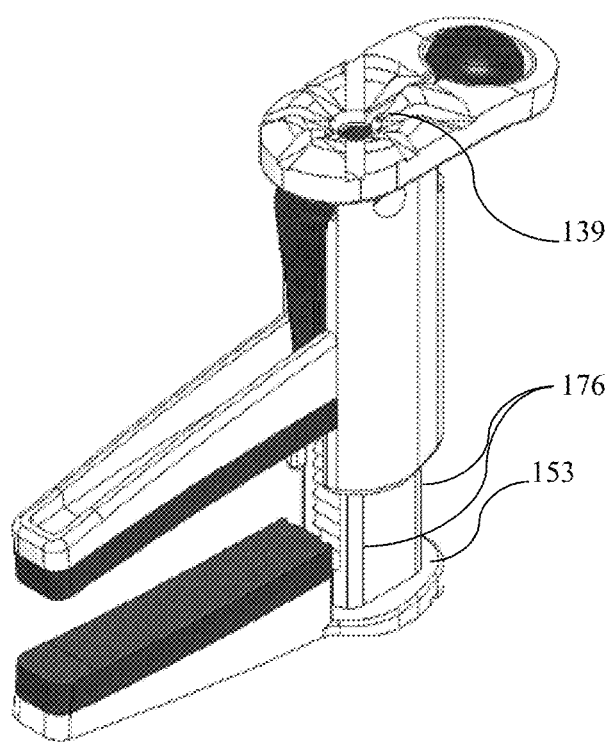
FIG. 2A is a side perspective view of another embodiment showing for markings for engaging with a tool or applicator such as, forceps.
Figure 2B:
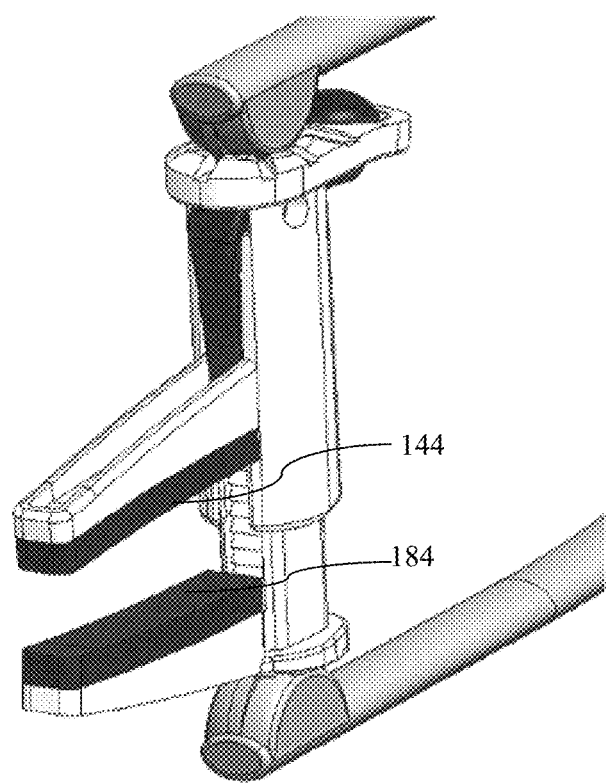
FIG. 2B shows a close up of the embodiment shown in FIG. 2A gripped by forceps.
Figure 2C:
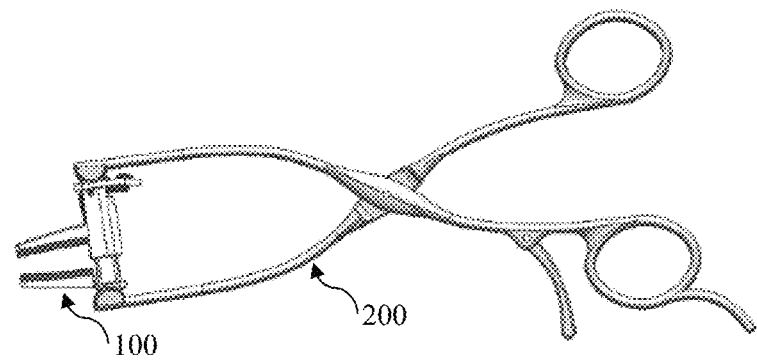
FIG. 2C shows a zoomed out view of the embodiment shown in FIG. 2A showing the forceps in full.
Figure 2D:
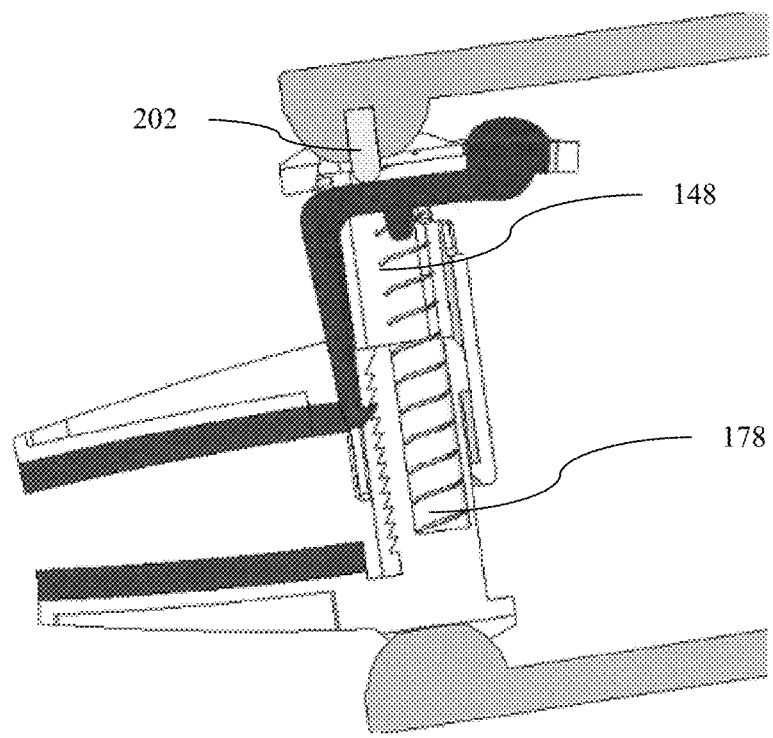
FIG. 2D shows a cross section showing a side view of the embodiment shown in FIGS. 2A, 2B and 2C.
Figure 2E:
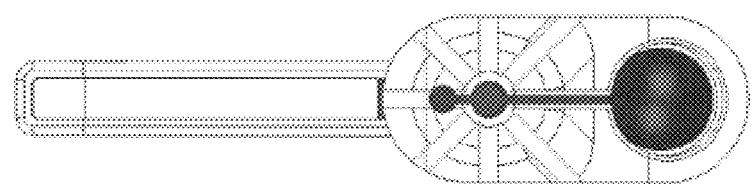
FIG. 2E shows a top view of the embodiment shown in FIGS. 2A, 2B, 2C and 2D.

FIG. 2E shows a top view of clamp 100 in which markings 139 can be seen for effective engagement with a tool.

Top jaw housing 110 also comprises a top bias retaining surface 114. Although shown to be comprised on lever 120, top bias retaining surface 114 may be comprised on any component of the top jaw housing 110 such as, the top base 112 and lever 120.

To keep spring 196 in position, top jaw housing 110 also comprises a top retainer 118. The top retainer 118 is shown to be raised to secure spring 196 in position. Top retainer 118 may be comprised on any component of top jaw housing 110 such as, the top base 112 and, as shown, lever 120. As shown, top retainer 118 forms part of the top bias retaining surface 114.

To aid gripping and prevent slippage, bottom exterior surface 156 also comprises a gripping surface 159.

Bottom jaw housing 150 comprises a bottom base 152 located on an end or a side of bottom jaw housing 150. Bottom base comprises a shoulder 153.

Bottom jaw housing 150 comprises a bottom bias retaining surface 154. Although not visible in the Figures, in the embodiment shown bottom bias retaining surface 154 is comprised on bottom base 152.

Bottom jaw housing 150 also comprises a bottom retainer 158 (not shown) which is also be raised to secure spring 196 in position. Bottom retainer 158 is shown to be comprised on the bottom base 152 and to form part of the bottom bias retaining surface 154.

Top jaw housing 110 comprises a top wall 130. Top wall 130 comprises an open slot 132 for the lever to access the rack. The top wall 130 may comprise a top wall upper surface 134.

Top jaw housing 110 also comprises a push tab 113. Push tab 113 extends out for easy gripping by a hand or finger. Push tab 113 also comprises one or more of a gripping surface, grooves and/or a marking for engaging with a tool or applicator such as, forceps 200.

Bottom jaw housing 150 comprises a bottom wall 170. Rack 160 is shown to be disposed on bottom wall 170. Bottom wall 170 comprises a bottom wall upper surface (not shown).

Top wall 130 and bottom wall 170 may be cylindrically shaped or generally cylindrically shaped; square shaped or generally square shaped; rectangularly shaped or generally rectangularly shaped, triangularly shaped or generally triangularly shaped; ovoid or generally ovoid shaped. From the teaching herein, a skilled person is readily able to select a suitable shape for top 130 and bottom 170 walls.

Top wall 130 and bottom wall 170 define a respective internal cavity or void 148, 178. As shown in the Figures, top wall 130 and bottom wall 170 are continuous or substantially continuous. A person of skill in the art is readily able to select a suitable structure for walls 130, 170.

The shoulder 153 of bottom jaw housing 150 also provides a push tab 155 which extends out for easy gripping by a hand or finger.

The top wall 130 and bottom wall 170 move along each other's length. In the embodiment shown, top wall 130 moves inside bottom wall 170. In other embodiments, bottom wall 170 moves inside the top wall 130. In the embodiment shown the movement is telescopic. The movement of the top wall 130 and bottom wall 170 is delimited by top wall upper surface 134 abutting shoulder 153. In other embodiments other structures or components of housings 110, 150 may delimit movement.

Top wall 130 and bottom wall 170 comprise a complementary shape to aid the movement along each other's length. The complementary shape may comprise one or more ridge 176 and slot 136. In the embodiment shown in FIGS. 1 and 2, ridges 176 are comprised on the bottom wall 170 and slots 136 (not shown) in top wall 130. In other embodiments the slots 136 may be comprised in the bottom wall 170 and the ridges 176 comprised in the top wall 130. The one or more ridge 176 and slot 136 may also prevent rotation of the top wall 130 with respect to the bottom wall 170.

Lever 120 is shown to comprise an axial arm 126 and a lateral arm 124. The axial arm 126 extends from the lateral arm 124. The axial arm 126 extends in a direction between the top jaw housing 110 and the bottom jaw housing 150. The lateral arm 124 extends in a direction of the top jaw 140 and bottom jaw 180. The lateral arm 124 and axial arm 126 may be disposed orthogonally or at an angle to each other. In the embodiment shown, the angle is a right angle or substantially a right angle. In other embodiments the angle may be 80; 81; 82; 83; 84; 85; 86; 87; 88; 89; 90; 91; 92; 93; 94; 95; 96; 97; 98; 99; 100 or less than 80 or more than 100 degrees. The axial arm 126 comprises one or more tooth or pawl 128. The lateral arm 124 comprises a button 122 disposed on a distal end 129 of lateral arm 124. Pressing button 122 on the distal end 129 pivots or moves axial arm 126 obliquely. The pivoting or oblique movement disengages the one or more tooth 128 from rack 160.

Button 122 is a region of lever 120 of increased width to assist in applying the force required to pivot or move lever 120.

In the embodiment shown lever 120 is an integral component comprising the lateral arm 124, axial arm 126 and the button 122 in one piece. In other embodiments, the components of lever 120 may be comprised on separate inter-fitting components.

Advantageously, the force applied by the bias 194 may be selectable. This is of significant advantage because it allows a series of clamps 100 to be provided that have different clamping force by virtue of employing different biases. This allows a readily selectable choice of clamping force. To readily identify clamps 100 with differing clamping forces, different colours may be used.

In the embodiment shown in the Figures, bias 194 comprises a spring 196. In other embodiments, bias 194 may comprise a foam. Spring 196 comprises a coiled spring. The foam may comprise an open-cell or closed-cell foam. The bias 194 may comprise a pre-set clamping force. The spring 196 and/or foam may be provided with a desired amount of bias force. The coefficient of stiffness of compliance of the spring and/or foam may be selectable.

Figure 1H:
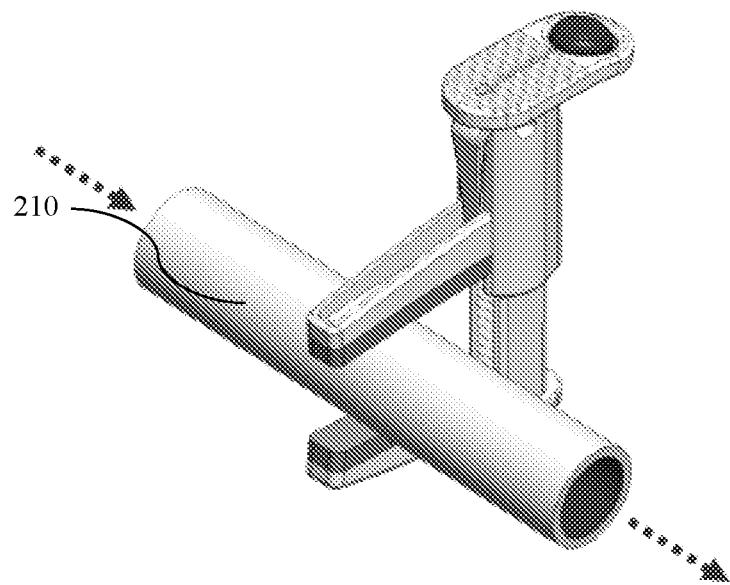
FIG. 1H is a top perspective view showing the same embodiment with a blood vessel positioned between the open jaws.
Figure 1I:
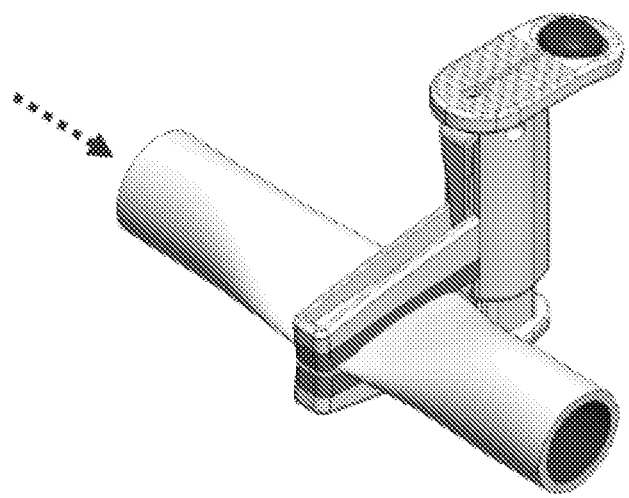
FIG. 1I is a top perspective view showing the same embodiment with a blood vessel clamped between the closed jaws.

The clamping of a blood vessel 210 between jaws 140, 180 is shown in the transition between the open configuration of jaws 140, 180 shown in FIG. 1H and the closed configuration of FIG. 1I. The arrows in FIG. 1H illustrate that in the open configuration, no clamping is applied to vessel 210 and blood flow is possible through the extent of the vessel 210. The single arrow in FIG. 1I illustrates that with the blood vessel 210 positioned between closed jaws 140, 180 no blood flow is possible past clamp 100.

Lever 120 is disposed to be moved by downward or angled force applied to the body 102 or top jaw 110 housing. The downward or angled force applied to the body 102 or top jaw housing 110 may comprise the downward force applied to cause graduated closing movement of the top jaw housing 110 and the bottom jaw housing 150.

As shown in the FIG. 1, each of the pair of jaws 140, 180 extend, in parallel, from the two piece body 102 and each of the pair of jaws 140, 180 comprise an elongate section 142, 182. Each of the pair of jaws 140, 180 may comprise a gripping surface 144, 184 which is the surface that makes contact with the substrate, e.g. blood vessel 210, being clamped.

Each jaw 140, 180, 440, 482, 540, 584 may comprise one or more atraumatic material. The atraumatic material may be disposed on the gripping surface 144, 184, 444*a*, 486*d*, 544*d*, 588*a*. In one embodiment, the one or more atraumatic material comprises an elongate cushion. In other embodiments, atraumatic material comprises one or more of a hydraulic cushion, a pneumatic cushion, a gel, a foam, a rubber, a sponge, a cloth, a flexible material, a flexible material with a closed cavity pre-filled with air, fluid or gel or other cushioning to prevent or reduce trauma. The atraumatic material may comprise one or move bevel. The atraumatic material may be moulded into the jaw or may be replaceable and/or interchangeable.

As a further safety feature, atraumatic material may comprise a coating to prevent slippage of the blood vessel, tissue or other body part clamped.

Figure 3A:
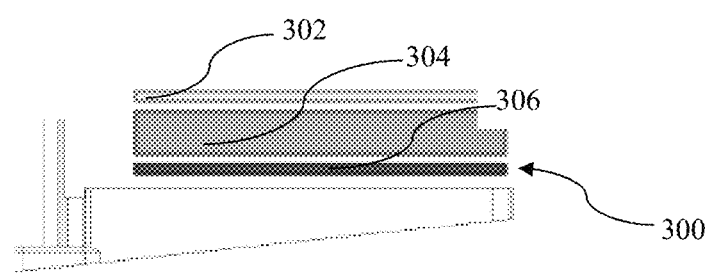
FIGS. 3A to 3G are schematic diagrams showing different embodiments of an atraumatic insert for the jaws.

FIGS. 3A to 3G show various embodiments of atraumatic material that may be utilised with any one of the embodiments of the invention. FIG. 3A shows an embodiment having an outer texture layer 302 a middle compliant layer 304 and an inner fixative layer 306. The texture layer 302 may comprise a mesh, a pattern or grooves. The compliant material 304 may comprise one or more of a silicone foam, silicone overmold, extruded silicone inserts and/or springs built into the jaw. The fixative layer 306 may comprise one or more adhesive such as, a liquid adhesive, a pressure sensitive adhesive, an overmold and/or a snap. The liquid adhesive may comprise one or more of a heat cure epoxy, a UV cure epoxy and a cyanoacrylate.

Figure 3B:
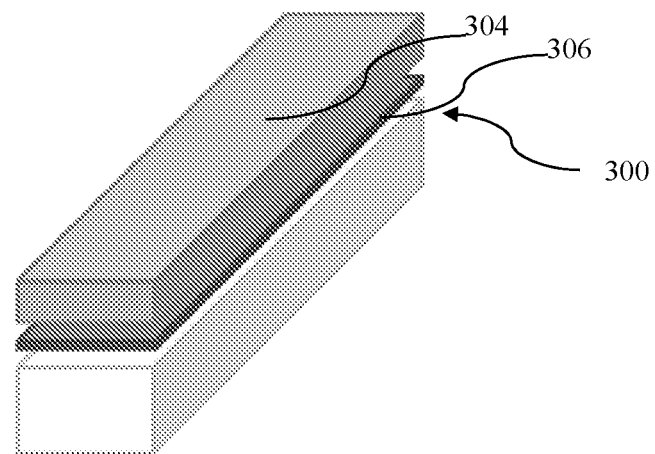

The embodiment show in FIG. 3B comprises a die cut foam. In other embodiments the foam may be waterjet or laser cut. FIG. 3B shows outer layer to be the complaint layer 304 to comprise two layers, an outer layer of a natural foam surface texture and an inner layer of silicone foam comprising a closed cell. The fixative layer 306 comprises any suitable adhesive. Prototypes have been made with this structure which has the advantages of being simple to manufacture with no tooling investment required. The disadvantages include that the grip may not be sufficient and it may be labour intensive to assemble.

Figure 3C:
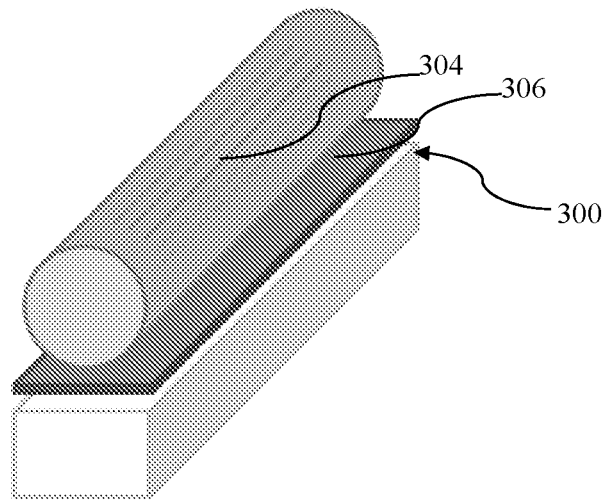

The embodiment shown in FIG. 3C comprises an extruded foam. The outer layer is the compliant layer 304 and comprises a natural material surface texture or may comprise texture grooves extruded therein. The compliant layer 304 may also comprise a mesh similar to that used in a Stealth Clip. The compliant layer 304 material may comprise a foam or low durometer silicone. While FIG. 3C shows compliant layer 304 to comprise a circular section in cross-section, from the teaching herein a skilled person is readily able to select a suitable shape such as, semi-circular or quadrilateral. The embodiment of FIG. 3C is simple to manufacture and also has a low tooling investment cost. Like the embodiment shown in FIG. 3B, disadvantages of the embodiment shown in FIG. 3C include the grip may not be sufficient and labour intensive to assemble.

Figure 3D:
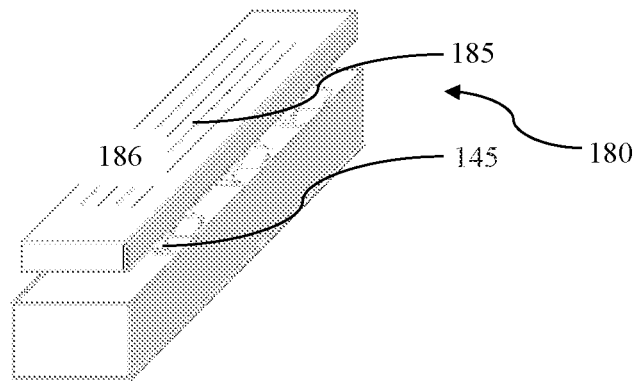

The embodiment shown in FIG. 3D does not comprise any of layers 302, 304, 306, Instead grip features 145, 185 are moulded directly into gripping surface 144, 184. Additionally, springs 146, 186 are moulded into jaws 140, 180 to give compliance to the vessel contact surface. The compliance jaw comes from the thin geometry of the plastic springs 146, 186. The embodiment shown in FIG. 3D is advantageously simple, it is possible to provide well resolved grip features 145, 185, no assembly of jaws 140, 180 is required and no additional material is required as layers 302, 304, 306 are absent. However, tooling investment may be higher and the part design may be more complicated.

Figure 3E:
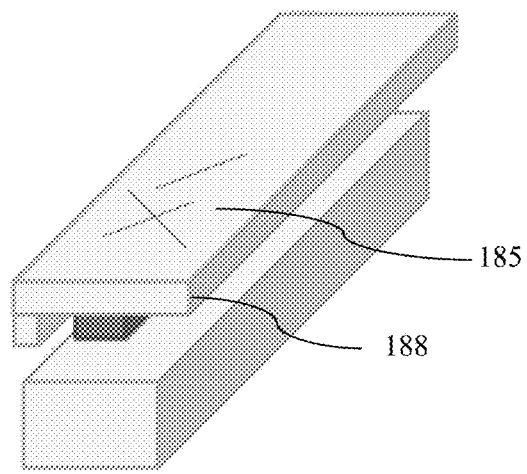
Figure 3F:
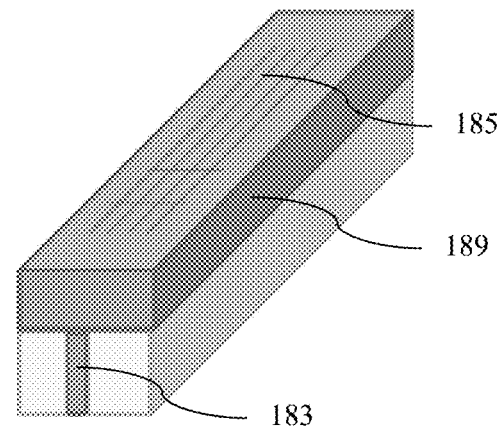
Figure 3G:
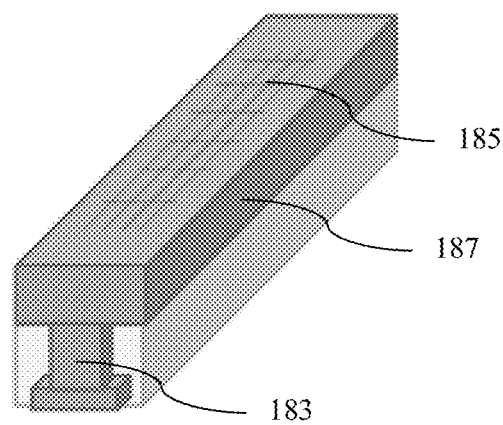
Figure 4A:
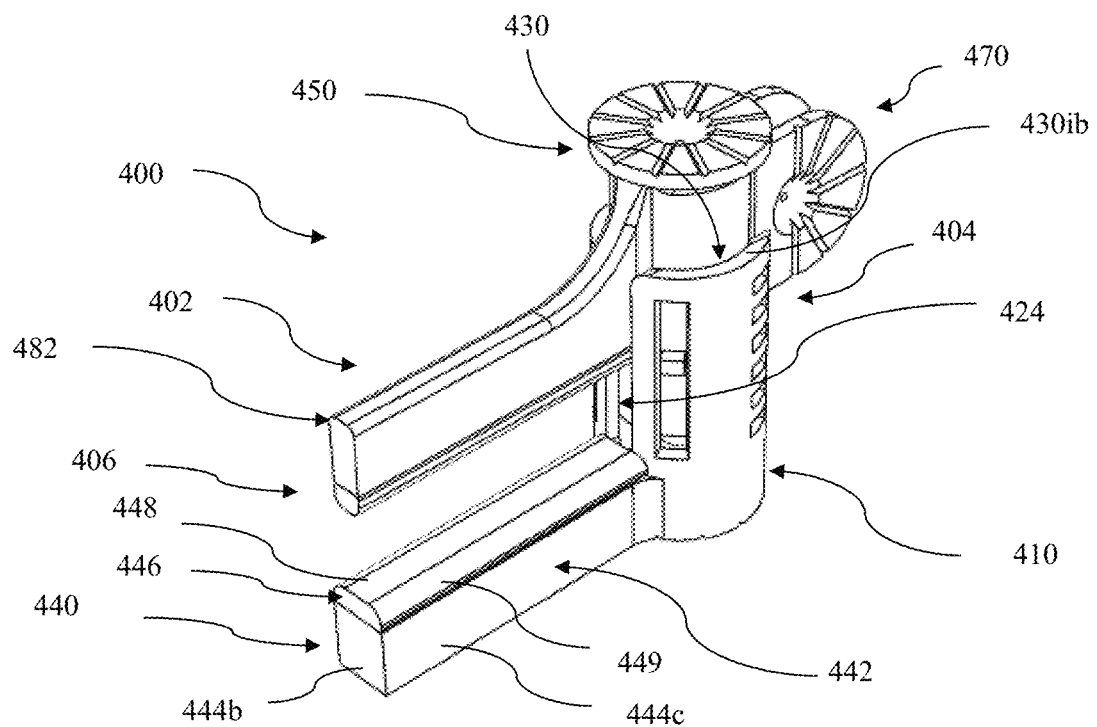
FIG. 4A is a side perspective view of one embodiment of a surgical clamp according to the invention in an open configuration.
Figure 4B:
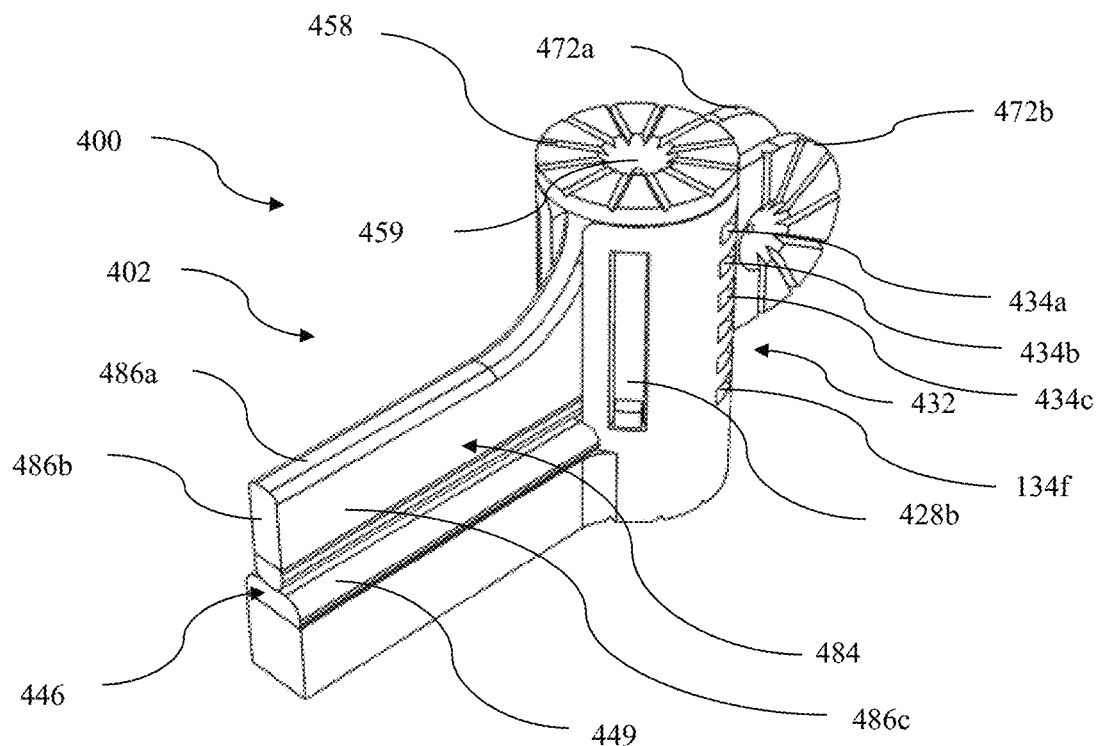
FIG. 4B is a side perspective view of the embodiment shown in FIG. 4A in a closed configuration.
Figure 4C:
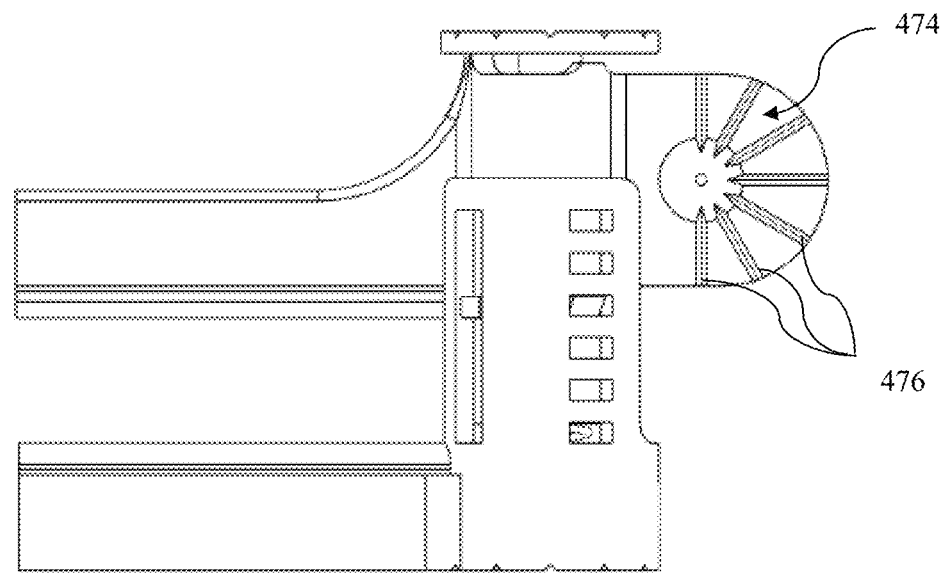
FIG. 4C is a side view of one embodiment of a surgical clamp according to the invention in an open configuration.
Figure 4D:
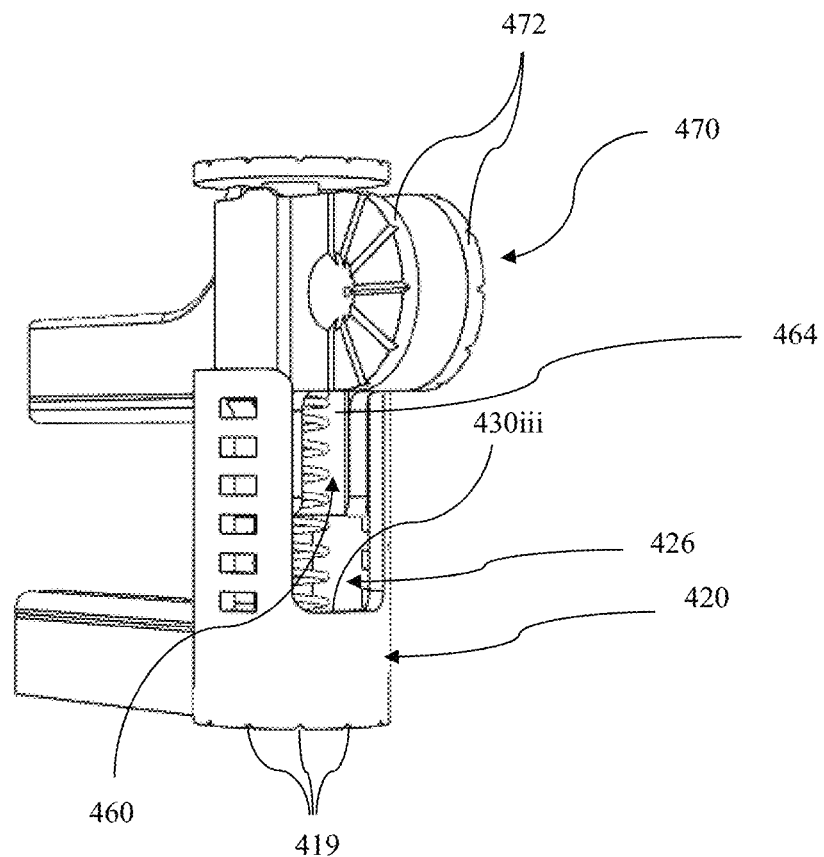
FIG. 4D is a rear perspective view of one embodiment of a surgical clamp according to the invention in an open configuration.

The embodiment shown in FIG. 3E comprises a rigid cap 148, 188 that clips onto jaws 140, 180. A compliant layer 304 of foam is disposed between the cap 148, 188 and jaw 140, 180 to provide cushioning. While cap 148, 188 is clipped on, it is free to move in the Z-direction to provide cushioning. As shown, caps 148, 188 also comprise grip features 145, 185. With this embodiment, well resolved grip features 145, 185 are possible.

The embodiment shown in FIG. 3D comprises an overmold 149, 189 comprised of silicone bonded through attachment feature 143, 183. Overmold 149 is also shown to comprise grip features 145, 185. Although disposed to have a flat gripping surface 144, 184, from the teaching provided herein, overmould 149, 189 may be provided with any suitable shape on gripping surface 144, 184 such as, curved or partially curved. This embodiment is also simple, does not require any adhesive, no bonding step is required which means simplified assembly. There is also a reduced risk of delamination.

The embodiment shown in FIG. 3E comprises a pad insert 147, 187 that is inserted by sliding or snapping into place. The insert 147, 187 may be comprised of molded silicone or comprise an extrusion. Insert 147, 187 is also shown to comprise grip features 145, 185. Although disposed to have a flat gripping surface 144, 184, from the teaching provided herein, insert 147, 187 may be provided with any suitable shape on gripping surface 144, 184 such as, curved or partially curved. This embodiment is also simple, does not require any adhesive, no bonding step is required which means simplified assembly. There is also a reduced risk of delamination.

In the embodiment shown in FIGS. 1A to 1I and 2A to 2E (FIGS. 1 and 2) each of the pair of jaws 140, 180 and/or atraumatic material are straight. In other embodiments they may be concave. The concave jaws and/or pads may be sized and shaped to conform to vasculature being clamped. In a preferred embodiment, the jaws 140, 180 are aligned with each other.

The embodiment shown in FIGS. 1 and 2 also shows each of the pair of jaws 140, 180 to have a similar or same size. In another embodiment, one of the jaws 140, 180 is wider or longer than the other 180, 140.

As shown in FIGS. 1 and 2, surgical clamp 100 is not elongate. Instead clamp 100 is unelongated, stout, squat or tubby. Surgical clamp 100 is substantially or generally block shaped. The shape of clamp 100 is such that pair of jaws 140, 180 comprise its predominate length.

From the above description it is clear that surgical clamp 100 is a mechanical clamp and does not comprise any electronic or electromechanical components.

As a further safety feature, one or more or each exposed surface of the clamp 100 may comprise a bevel or other safety feature to minimise the likelihood of trauma.

The relative movement of the pair of jaws 140, 180 comprises up and down movement or side to side movement. The relative movement may comprise one of the pair of jaws 140, 180 moving relative to the other or both moving.

The invention also provides a method of clamping a blood vessel, tissue or other body part with clamp 100.

Also provided by the invention is a method of manufacturing clamp 100.

In use, the entire surgical clamp 100 remains inside the subject. To reduce or to minimise the likelihood of trauma, one or more or each exposed surface of clamp 100 may comprise a bevel or other safety feature.

Clamp 100 may be used to clamp a blood vessel, tissue or other body part. In a particular embodiment, surgical 100 clamp is a haemostatic clamp but is not so limited.

Surgical clamp 100 may be used in laparoscopic or keyhole surgery in which a tool or applicator such as, forceps 200, is used to engage with one or more of markings 139, 179 as required.

Clamp 100 may be comprised of any suitable surgical grade material such as, but not limited to, one or more of silicone, a polymer or a metal.

Although not shown, surgical clamp 100 may comprise a visibility or locatory feature such as a high-vis colour.

From the teaching herein, a skilled person understands that surgical clamp 100 may be used with any suitable animal. While not limited thereto, the animal may be a mammal and the mammal may be a human. Surgical clamp 100 may also be used with a companion animal such as, a canine or a feline, livestock such as, an equine, a bovine, an ovine, a porcine, a hircine.

Advantageously, clamp 100 provides graduated clamping and thereby provides more control over the clamping force applied. This has the advantage of reducing the likelihood of damage to the blood vessels, tissue or other body part and reducing the likelihood of plaque dislodgement.

Conventional surgical clamps have been shown to cause damage to the internal endothelial layer of blood vessels. Advantageously, the present invention provides graduated clamping which reduces the likelihood of this type of damage.

Advantageously, the present invention provides graduated clamping and gives the health care professional control over the force applied to effect the clamping. This is in stark contrast to prior art clamps that do not give the health care professional any control over clamping. With conventional "all or nothing" clamps, the user must apply the closing force that is predetermined by the clamping mechanism provided in the clamp. With other prior art devices that clamp via elongate shafts or handles, it is difficult to estimate or adjust the clamping force because the actuator is distal from the site of clamping and a large amount of leverage may be utilised.

By having the top and bottom housings 110, 150 adjacent to pair of jaws 140, 180, clamp 100 may give the user more feedback and "feel" of the clamping force due to the lack of mechanical advantage. This is another advantage of the present invention over conventional forceps/scissor type applicators.

A further advantage of the present invention is that adjustments to the amount of clamping force can be easily made by manipulating lever 120. That this can be done without moving the fingers or hands is of further significant advantage.

Feedback provided by a surgeon on a prototype device was that the feel or tactile sensation provided by the graduated opening and closing afforded by the present invention was greatly pleasing.

Advantageously, the clamp 100 of the present invention is easy to use and allows graduated opening and closing with tactile feedback given to the user by the bias and any resistance provided by the vessel.

The amount of force can be controlled by a user to affect a desired amount of opening or closing. A light pressing will open only one notch, while more force will provide complete opening or closing.

FIG. 4 (FIGS. 4A; 4B; 4C; 4D; 4E; 4F; and 4G; or FIGS. 4A to 4G) shows another embodiment of a surgical clamp 400 according to the invention. Clamp 400 comprises a two-piece body 402 comprising a mechanical device 404 and a pair of jaws 406. The mechanical operation of mechanical device 404 moves the pair of jaws 406 relative to each other to thereby effect a clamping of, for example, a blood vessel, tissue or other body part. The movement may comprise one of the pair of jaws 406 moving relative to the other or both moving.

In the embodiment shown in FIGS. 4A to 4G mechanical device 404 comprises a ratchet. However, the invention is not so limited. From the teaching herein, a skilled person is readily able to select other suitable mechanical devices to effect relative movement of the pair of jaws 406, for example, a rack and pinion or a damper.

In the illustrated embodiment utilizing a ratchet as the mechanical device 404, the two-piece body 406 comprises a rack housing 410 and a pawl housing 450. Both the rack housing 410 and pawl housing 450 are generally cylindrically shaped, with a jaw 440, 482 extending therefrom.

While housings 410, 450, wall 420 and rod 452 are shown in FIG. 4 to be cylindrically shaped, in other embodiment housings 410, 450, wall 420 and rod 452 may be square shaped or generally square shaped; rectangularly shaped or generally rectangularly shaped, triangularly shaped or generally triangularly shaped; ovoid or generally ovoid shaped or any other suitable shape. From the teaching herein, a skilled person is readily able to select a suitable shape for housings 410, 450 and thereby body 402, wall 420 and rod 452.

In the embodiment shown, pawl jaw 482 is disposed on a male housing, the pawl housing 450, and the rack jaw 440 is disposed on a female housing, the rack housing 410. The male pawl housing 450 and the female rack housing 410 move relative to each other to move the pair of jaws 406. In this way, the male pawl housing 450 and female rack housing 410 comprise the ratchet and pawl.

In another embodiment, pawl jaw 482 is disposed on a female housing, and the rack jaw 440 is disposed on a male housing.

The mechanical device 404 comprises a rack 432 comprised on rack housing 410 and a pawl 478 comprised on pawl housing 450. In this ratchet and pawl embodiment, the movement of the two-piece body 402 comprises linear motion. In the embodiment shown in the Figures, the housings 410, 450 move in an up and down motion, in other embodiments this is a side to side motion.

As shown in FIGS. 4A to 4G, the rack housing 410 comprises a base 412 which comprises a bias retaining surface 414 and an exterior surface 418. The bias retaining surface 414 comprises a retainer 416 to secure bias 494. To assist in securing the bias 494, the retainer 416 is raised from base 412 and comprises a projection.

Base 412 also comprises grooves 419 for grip and marking 417 (not shown) may engage with a tool or applicator such as, forceps, to allow pawl housing 450 to be moved up and down from a distal site. In this manner, base 412 may be in the form of a push tab.

In the embodiment shown in the Figures, base 412 is shown on the bottom of rack body 410. In another embodiment, base 412 is on a side of rack body 410.

Rack housing 410 comprises a wall 420 which comprises a cylindrical shape or generally a cylindrical shape. The wall 420 comprises opposing uprights 422(*a,b*) which are separated by a jaw channel 424 and an actuator channel 426. One or both of the opposing uprights 422(*a,b*) comprise or define a range slot 428(*a,b*).

Rack housing 410 comprises a top surface 430 which comprises upright top surface 430*i*(*a,b*), a jaw channel top surface 430*ii* and an actuator channel top surface 430*iii*, all three having different heights.

The upright top surface 430*i*(*a,b*) restricts movement of the two-piece body 402 by impeding travel of the pawl housing 450 by abutting push tab pawl housing base 454 at the extent of its downward motion.

The jaw channel top surface 430*ii* also restricts movement of the two-piece body 402. In this instance, by impeding one of the pair of jaws 406 (in the embodiment shown in FIGS. 4A to 4G, pawl jaw 482).

Another area that restricts movement of two-piece body 402 is actuator channel top surface 430iii, which restricts movement by impeding actuator 470.

The range slots 428(a,b) also restrict or guide movement of two-piece body 402. This is done by range slot top surface 436 and a range slot bottom surface 438 restricting movement by impeding locators 480(a,b). The inter-fitting of range slots 428(a,b) and locators 480(a,b) also prevent any twisting of the housings 410, 450 relative to one another during linear, up and down, motion to open and close pair of jaws 406.

In the embodiment shown in FIG. 4, rack housing 410 comprises two racks 432(a,b). Racks 432(a,b) are on opposing sides of rack housing 410, separated by and equidistant from jaw channel 424. In other embodiments, surgical clamp 400 may comprise one, two, three, four, five, six, seven, eight, nine, ten or more than ten racks 432.

In the embodiment shown in FIG. 4, each rack 432 comprises six fenestrations 434(a,b, c,d,e,f). In other embodiments, each rack 432 comprises one, two, three, four, five, seven, eight, nine, ten or more than ten fenestrations 434.

Rack housing 410 comprises one jaw, the rack jaw 440, of the pair of jaws 406 with the other jaw, the pawl jaw 482, comprised on pawl housing 450. Jaws 440, 482 may be integrally formed with housings 410, 450 in a one-piece molding, casting or other manufacturing process. Each jaw 440, 482 extends in parallel from the body 402.

Turning to pawl housing 450, a rod 452 is comprised in the form of an upright column. Rod 452 extends from base 454 and comprises rod wall 462. Rod wall 462 comprises a hollow channel 460 to accommodate bias 494 and cutaway 464 to achieve a desired range of motion.

The presence of cutaway 464 means that rod wall top surface 463 (not shown) and rod wall cutaway top surface 465 (not shown) are disposed at different heights.

As shown in FIGS. 4A to 4G, pawl housing 450 also comprises base 454 in the form of a push tab comprising a gripping surface 456 comprising grooves 458 and a marking 459. The marking 459 may engage with a tool or applicator such as, forceps, to allow pawl housing 450 to be moved up and down from a distal site. Pawl housing base 454 also comprises a bias retaining surface 466 which comprises a bias retainer 468 in the form of a post that is raised from base 454.

Pawl housing 450 also comprises an actuator 470 in the form of a handle which can be gripped to operate the clamping. The gripping of either the actuator 470 or the base 454 and exterior surface 418 may be by either hand or a tool or applicator such as, forceps.

In the embodiment shown in FIGS. 4A to 4G, actuator 470 comprises two flanges 472(a,b) which can be pressed or squeezed together to compress rod wall 462 such that pawls 478(a,b) withdraw from any rack fenestration 434 to allow pawl housing 450 to move relative to rack housing 410 and move jaws 440, 482 relative to one another. Each of the two flanges 472(a,b) comprise a gripping surface 474 and grooves 476 to reduce the likelihood of slippage. Each of the two flanges 472(a,b) also comprise a marking 483 for engaging with a tool or applicator such as, forceps, to allow the actuator 470 to be operated from a distal site.

Actuator 470 is shown located on a side of pawl housing 450. In another embodiment, actuator 470 may be located on a top or bottom of pawl housing 450. The positioning of actuator 470 adjacent cutaway 464 aids in the compression of rod wall 462 to withdraw pawls 478 (a,b) from rack fenestration 434.

The pawls 478(a,b) are shown comprised on rod 452 and integral with rod wall 462. In the embodiment shown in FIG. 4, pawl housing 450 comprises two pawl 478(a,b) disposed on opposing sides of rod 452 and separated by jaw 482 and actuator 470. Each of the pawls 478(a,b) are dimensioned to fit within each of the rack fenestrations 434(a-f).

Also located between the two pawls 478(a,b) are locators 480 (a,b) which are shown in the embodiment depicted in FIG. 4 to be in the form of a protuberance dimensioned to fit within respective range slots 428(a,b). In the embodiment of the Figures, there is a locator 480(a,b) on each side of pawl jaw 482, between pawl jaw 482 and pawls 478(a,b).

Each of the pair of jaws 406 extend from the two piece body 402. The pair of jaws 406 are aligned with each other. The rack jaw 440 is integral with the rack housing 410 and the pawl jaw 482 is integral with the pawl housing 450. Each jaw 440, 482 comprises an elongate section 442, 484 comprising a top surface 444a (not shown), 486a, a front surface 444b, 486b, side surfaces 444c, 486c and a bottom surface 444d, 486d (not shown). A pad 446, 488 is disposed on a gripping surface of each jaw 440, 482. The gripping surface of each jaw 440, 482 is that surface contacting the other jaw, i.e. the bottom surface 486d of pawl jaw 482 and the top surface 444a of rack jaw 440. Pads 446, 488 may be moulded into jaw 440, 482 or may be replaceable and/or interchangeable.

When clamping a blood vessel, tissue or other body part, the gripping surfaces 486d, 444a and pads 446, 488 may not make contact with each other or may only contact along a part of their length.

The pads 446, 488 comprise an elongate cushion 490 that has a bevel 449, 492.

Each pad 446, 488 may comprise a hydraulic cushion, a pneumatic cushion, a gel, a foam, a rubber, a sponge, a cloth, a flexible material, a flexible material with a closed cavity pre-filled with air, fluid or gel or other cushioning to prevent or reduce trauma.

Although not shown, each pad 446, 488 may further comprise a coating to prevent slippage of the blood vessel, tissue or other body part clamped.

While each of the pair of jaws 406 is shown to be straight, in another embodiment, the gripping surface 486d, 444a and/or the pads 446, 488 is concave. The concave pair of jaws 406 and/or pads 446, 488 may be sized and shaped to conform to a blood vessel, tissue or other body part being clamped.

In the embodiment shown, rack jaw 440 is shown to be wider than pawl jaw 482. In other embodiments, the jaws 440, 482 have a similar or same size or pawl jaw 482 is wider than rack jaw 440.

The shape of surgical clamp 400 is unlike many conventional elongate or scissor-shaped clamps. In these conventional elongate clamps, the actuator or handle is distal to the clamping jaws and separated by elongate components. In contrast, surgical clamp 400 comprises an actuator 470 that is proximal, adjacent and/or adjoins the pair of jaws 406. This adjoining is without any elongate spacing.

To be clear, surgical clamp 400 is not elongate and is instead, unelongated, stout, squat or tubby. Instead, surgical clamp 400 is substantially or generally block shaped. The rack jaw 440 and pawl jaw 482 comprise the predominate length of clamp 400.

The body 402 and each of the rack housing 410 and pawl housing 450, which interfit to form two-piece body 402, are cylindrical or substantially cylindrical in shape with rod-shaped jaws 440, 482 extending therefrom.

Clamp 400 further comprises a bias 494 which in the embodiment shown comprises spring 496 in the form of a coil spring. From the teaching herein, a skilled person is able to select another mechanical device to generate the clamping force such as, a foam including an open-cell foam and a closed-cell foam. The bias 494 may be selected to produce a minimum force for opening.

Clamp 400 provides graduated movement and/or clamping force and clamping distance by using actuator 470 to select a desired one of rack fenestration 434a-f.

In use, the entire surgical clamp 400 remains inside the subject. To reduce or to minimise the likelihood of trauma, one or more or each exposed surface of clamp 400 may comprise a bevel or other safety feature.

From the above description it is clear that surgical clamp 400 is a mechanical clamp and does not comprise any electronic or electromechanical components.

Clamp 400 may be used to clamp a blood vessel, tissue or other body part. In a particular embodiment, surgical 400 clamp is a haemostatic clamp but is not so limited.

Surgical clamp 400 may be used in laparoscopic or keyhole surgery in which a tool or applicator such as, forceps, is used to engage with one or more of markings 417, 459, 477 as required.

The invention also provides a method of manufacturing clamp 400. Clamp 400 may be comprised of any suitable surgical grade material such as, but not limited to, one or more of silicone, a polymer or a metal.

Although not shown, surgical clamp 400 may comprise a visibility or locatory feature such as a high-vis colour.

From the teaching herein, a skilled person understands that surgical clamp 400 may be used with any suitable animal. While not limited thereto, the animal may be a mammal and the mammal may be a human. Surgical clamp 400 may also be used with a companion animal such as, a canine or a feline, livestock such as, an equine, a bovine, an ovine, a porcine, a hircine.

Advantageously, clamp 400 provides graduated clamping and thereby provides more control over the clamping force applied. This has the advantage of reducing the likelihood of damage to the blood vessels, tissue or other body part and reducing the likelihood of plaque dislodgement.

Conventional surgical clamps have been shown to cause damage the internal endothelial layer of blood vessels. Advantageously, the present invention provides graduated clamping which reduces the likelihood of this type of damage.

Advantageously, the present invention provides graduated clamping and gives the health care professional control over the force applied to effect the clamping. This is in stark contrast to prior art clamps that do not give the health care professional any control over clamping. With conventional "all or nothing" clamps, the user must apply the closing force that is predetermined by the clamping mechanism provided in the clamp. With other prior art devices that clamp via elongate shafts or handles, it is difficult to estimate or adjust the clamping force because the actuator is distal from the site of clamping and a large amount of leverage may be utilised.

By placing actuator 470a,b adjacent to pair of jaws 406, clamp 400 may give the user more feedback and "feel" of the clamping force due to the lack of mechanical advantage. This is another advantage of the present invention over conventional forceps/scissor type applicators.

As used herein an "open cell foam", also known as reticulated foam, is a porous, low density solid foam. Open cell foams are open foams i.e. there are few, if any, intact bubbles or cell windows. The solid component of an open cell foam may be an organic polymer like polyurethane, a ceramic or a metal. These materials have a high porosity and large surface area.

Figure 5A:
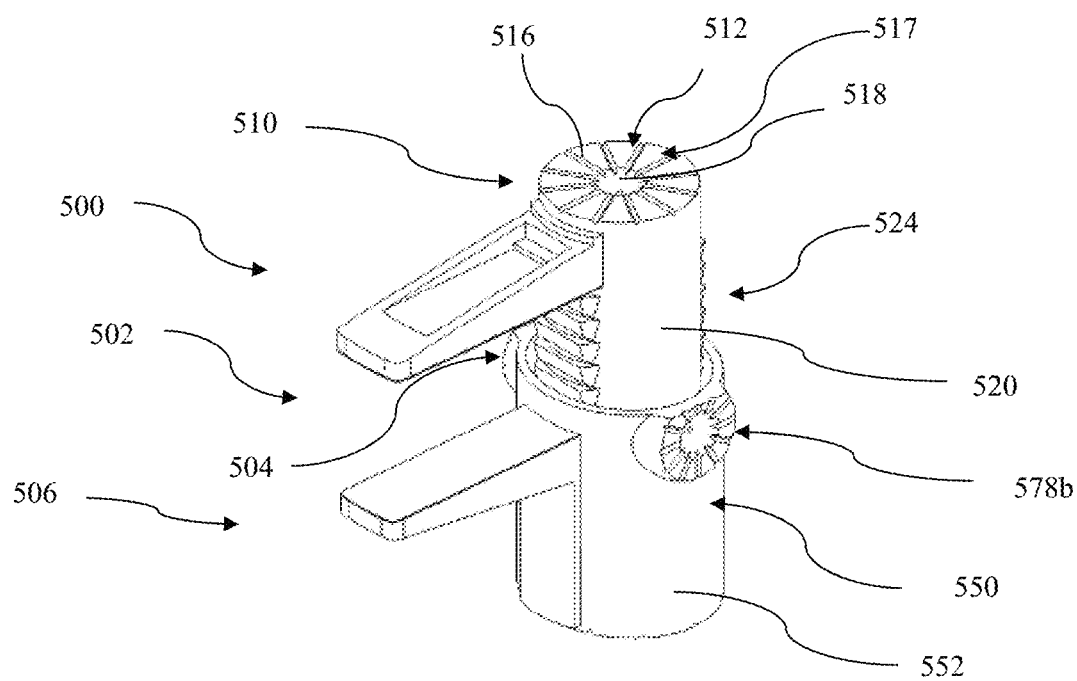
FIG. 5A is a side perspective view of one embodiment of a surgical clamp according to the invention in an open configuration.
Figure 5B:
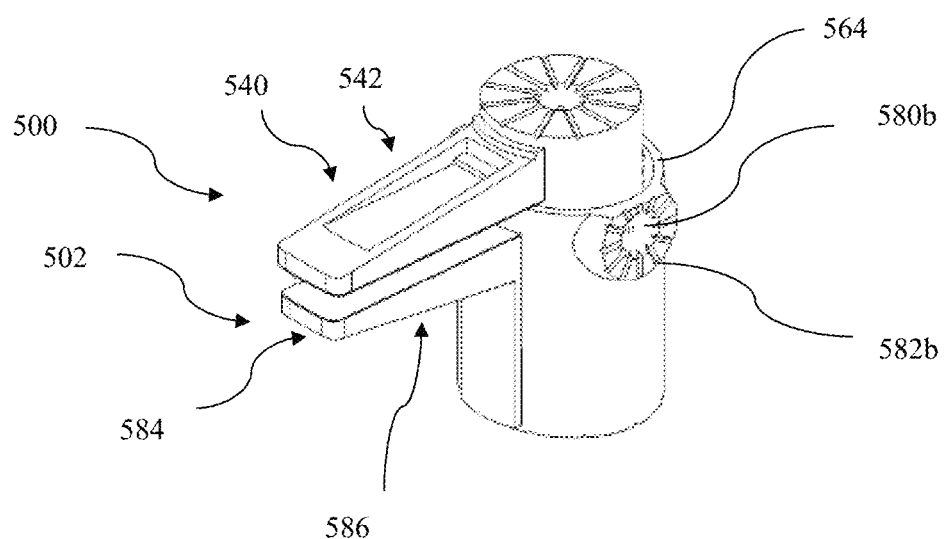
FIG. 5B is a side perspective view of the embodiment shown in FIG. 5A in a closed configuration.
Figure 5C:
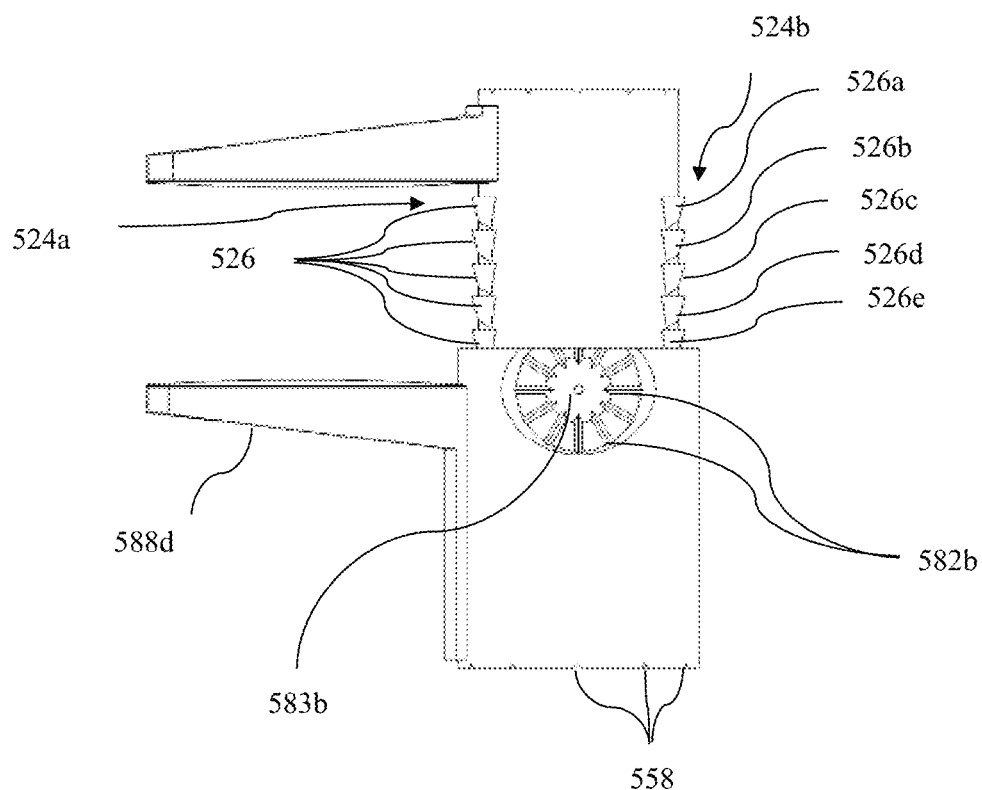
FIG. 5C is a side view of one embodiment of a surgical clamp according to the invention in an open configuration.
Figure 5D:
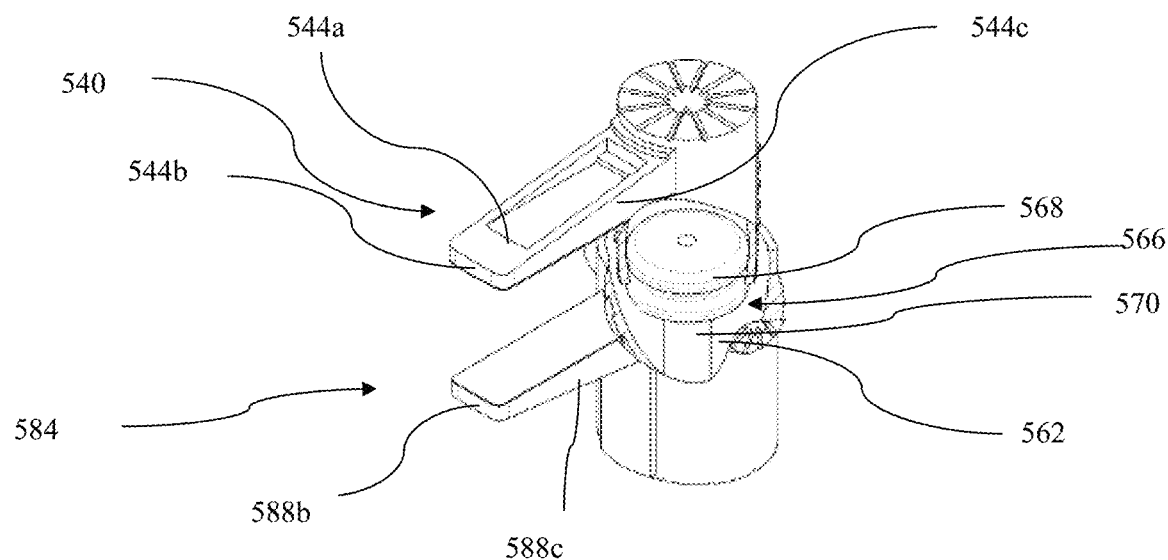
FIG. 5D is a perspective view with partial cutaway of one embodiment of a surgical clamp according to the invention in an open configuration.

FIG. 5 (FIGS. 5A; 5B; 5C; 5D; 5E; 5F; 5G; and 5H; FIGS. 5A to 5G) shows one embodiment of a surgical clamp 500 according to the invention. Clamp 500 comprises a two-piece body 502 comprising a mechanical device 504 and a pair of jaws 506. The mechanical operation of mechanical device 504 moves the pair of jaws 506 relative to each other to thereby effect a clamping of, for example, a blood vessel, tissue or other body part. The movement may comprise one of the pair of jaws 506 moving relative to the other or both jaws 540, 584 moving.

In the embodiment shown in FIGS. 5A to 5H, mechanical device 504 comprises a ratchet and pawl. However, the invention is not so limited. From the teaching herein a skilled person is readily able to select other suitable mechanical devices to effect relative movement of the pair of jaws 506, for example, a rack and pinion or a damper.

In the illustrated embodiment of FIG. 5 utilizing a ratchet and pawl as the mechanical device 504, the two-piece body 502 comprises a rack housing 510 and a pawl housing 550. Both the rack housing 510 and pawl housing 550 are generally cylindrically shaped, with a jaw 540, 584 extending therefrom.

While housings 510, 550, rack housing wall 520 and pawl housing wall 552 are shown in FIG. 5 to be cylindrically shaped, in other embodiment housings 510, 550 and walls 520, 552 may be square shaped or generally square shaped; rectangularly shaped or generally rectangularly shaped, triangularly shaped or generally triangularly shaped; ovoid or generally ovoid shaped or any other suitable shape. From the teaching herein, a skilled person is readily able to select a suitable shape for housings 510, 550 and thereby body 502 and walls 520, 552.

In the embodiment shown, rack jaw 540 is disposed on a male housing, the rack housing 510, and the pawl jaw 584 is disposed on a female housing, the pawl housing 550. The male rack housing 510 and the female pawl housing 550 move relative to each other to move the pair of jaws 506. In this way, the male rack housing 510 and female pawl housing 550 comprise the ratchet and pawl of mechanical device 504.

In another embodiment, rack jaw 540 is disposed on a female housing, and the pawl jaw 582 is disposed on a male housing.

The mechanical device 504 comprises a rack 524 comprised on rack housing 510 and teeth 576 comprised on pawl housing 550. In this ratchet and pawl embodiment, the movement of the two-piece body 502 comprises linear motion. In the embodiment shown in the Figures, the housings 510, 550 move in an up and down motion, in other embodiments the movement is a side to side motion.

As shown in FIGS. 5A to 5H, rack housing 510 comprises a base 512 which comprises a bias retaining surface 514 and an exterior surface 516. The bias retaining surface 514 comprises a retainer 515 to assist in securing bias 594. To assist in securing the bias 594, the retainer 515 is raised from base 512 and comprises a projection.

Base 512 also comprises grooves 517 for grip and marking 518 may engage with a tool or applicator such as, forceps, to allow the rack housing 510 to be moved up and down from a distal site. In this manner, base 512 may be in the form of a push tab.

In the embodiment shown in FIG. 5, base 512 is shown on the bottom of rack housing 510. In another embodiment, base 512 is on a side of rack housing 510.

Rack housing 510 comprises a wall 520 which comprises a cylindrical shape or generally a cylindrical shape. Wall 520 comprises a rim 522 which is planar.

Rack housing wall 520 defines rack housing reservoir 528 in which bias 594 is retained. As will be elucidated below, reservoir 528 also retains fluid 507 (not shown).

In the embodiment shown in FIG. 5, rack housing 510 comprises two racks 524(a,b). Racks 524(a,b) are on opposing sides of rack housing 510. A first rack 524a is aligned with rack jaw 540, in a front of rack housing 510, and the second rack 524b is on the opposing side of wall 520 at a rear of rack housing 510. In other embodiments, surgical clamp 500 may comprise one, two, three, four, five, six, seven, eight, nine, ten or more than ten racks 524.

Figure 5H:
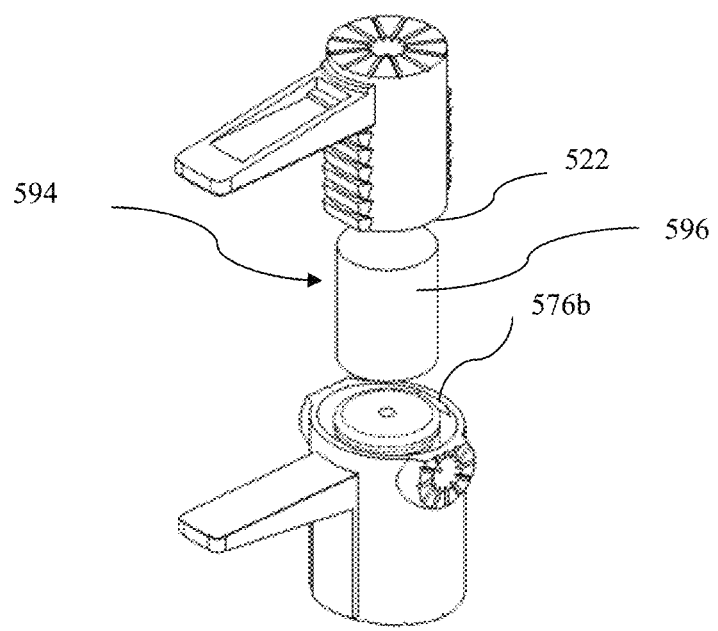
FIG. 5H is an exploded view of one embodiment of a surgical clamp according to the invention.

In the embodiment shown in FIG. 5, each rack 524a,b comprises six ridges 526a,b, c,d,e,f (524f not labelled but illustrated in FIGS. 5G and 5H). In other embodiments, each rack 524 comprises one, two, three, four, five, six, seven, eight, nine, ten or more than ten fenestrations 526.

Rack housing 510 comprises one jaw, the rack jaw 540, of the pair of jaws 506 with the other jaw, the pawl jaw 584, is comprised on pawl housing 550. Jaws 540, 584 may be integrally formed with housings 510, 550 in a one-piece molding, casting or other manufacturing process. Each jaw 540, 584 extends in parallel from the body 502.

Pawl housing 550 also comprises a wall 552 extending from pawl housing base 554. Pawl housing wall 552 is also shown to comprise a cylindrical shape or generally a cylindrical shape and a wall rim 564 which is also planar.

Pawl wall 552 defines pawl housing reservoir 562 in which a second bias 594 (not shown) can be accommodated. As will be elucidated below, reservoir 562 also retains fluid 507 (not shown).

As shown in FIGS. 5A to 5H, pawl housing 550 also comprises base 554 in the form of a push tab comprising a gripping surface 556 comprising grooves 558 and a marking 560. The marking 560 may engage with a tool or applicator such as, forceps, to allow pawl housing 550 to be moved up and down from a distal site. Pawl housing base 554 also comprises a bias retaining surface 572 which comprises a bias retainer 573 in the form of a protrusion raised from base 554.

Pawl housing 550 also comprises actuator 578 in the form of a pair of handles 578a,b which can be gripped to operate the clamping. The gripping of either the actuators 578a,b or the bases 512, 554 may be by either hand or a tool or applicator such as, forceps.

In the embodiment shown in FIGS. 5A to 5H, actuator 578a,b comprises flanges 580(a,b) which can be pressed or squeezed together to compress pawl wall 552 at the sides such that the front and back of wall 552 flexes outwardly causing teeth 576a,b (only 576b is shown, see FIG. 5H) to withdraw from racks 524 to allow pawl housing 550 to move relative to rack housing 510. This movement moves jaws 540, 584 relative to one another.

Each of the two flanges 580a,b comprise a gripping surface comprising grooves 582a,b to reduce the likelihood of slippage. Each of the two flanges 580a,b also comprise a marking 583a,b (only 583b is labelled, see FIG. 5C) for engaging with a tool or applicator such as, forceps, to allow the actuator 578 to be operated from a distal site.

An actuator 578 is shown located on each side of pawl housing 550. In another embodiment, the actuators 578 may be located on a top or bottom of pawl housing 550.

Teeth 576a,b (only one tooth 576b is shown at the rear of pawl housing 550, the front tooth 576b that mates with front rack 524 is not shown) are comprised on and integral with wall 552. In the embodiment shown in FIG. 5, pawl housing 550 comprises two teeth 576a,b disposed on opposing sides of rod wall 552 and separated by pawl jaw 584 and actuators 578a,b. Each of the teeth 576a,b are dimensioned to inter-fit with each of the rack ridges 526 a-f to prevent or at least resist movement without operation of handles 578a,b.

Each of the pair of jaws 506 extend from the two piece body 502. The pair of jaws 506 are aligned with each other. The rack jaw 540 is integral with the rack housing 510 and the pawl jaw 584 is integral with the pawl housing 550. Each jaw 540, 584 comprises an elongate section 542, 586 comprising a top surface 544a, 588a, a front surface 544b, 588b, side surfaces 544c, 588c and a bottom surface 544d, 588d. A pad 546, 590 is disposed on a gripping surface of each jaw 540, 584. The gripping surface of each jaw 540, 584 is that surface contacting or opposing the other jaw, i.e. the bottom surface 544d of rack jaw 540 and the top surface 588a of pawl jaw 584.

The pads 546,590 comprise an elongate cushion. Each pad 546, 590 also comprises a membrane 548,592 to provide the cushioned surface for clamping. The membranes 548, 592 comprise a soft and/or pliable material that is also non-porous. The membrane may comprise material selected to reduce the likelihood of damage to blood vessel, tissue or other body part clamped. The membrane may be comprised of any suitable medical grade material such as, silicon or polymeric material.

In the embodiment shown in FIG. 5, membranes 548,592 are attached at a jaw end to a flange 580 at a distal end of each jaw 540,584 and at a housing end to the rack housing 510 or pawl housing 550. In another embodiment, at a housing end, membranes 548,592 are attached to a proximal end of each jaw 540,584.

Each pad 546,590 may comprise a hydraulic cushion, a pneumatic cushion, a gel, a foam, a rubber, a sponge, a cloth or other cushioning to prevent or reduce trauma.

Each pad 546, 590 may also comprise a coating to prevent slippage of the blood vessel, tissue or other body part clamped. From the teaching herein, a skilled person is readily able to select a suitable coating from any conventional non-slip coating suitable for medical applications.

While each of the pair of jaws 506 is shown to be straight, in another embodiment, the gripping surface 544d, 588a and/or the pads 546, 590 are concave. The concave pair of jaws 506 and/or pads 546, 590 may be sized and shaped to conform to the blood vessel, tissue or other body part being clamped.

In the embodiment shown, rack jaw 540 and pawl jaw 584 are shown to have the same length and width and to have the same size. In other embodiments, one jaw 540, 584 is wider and/or longer than the other 584, 540.

The shape of surgical clamp 500 is unlike many conventional elongate or scissor-shaped clamps. In these conventional elongate clamps, the actuator or handle is distal to the clamping jaws and separated by elongate components. In contrast, surgical clamp 500 comprises an actuator 578 that is proximal, adjacent and/or adjoins the pair of jaws 506. This adjoining is without any elongate spacing.

To be clear, surgical clamp 500 is not elongate and is instead, unelongated, stout, squat or tubby. Instead, surgical clamp 500 is substantially or generally block shaped. The rack jaw 540 and pawl jaw 584 comprise the predominate length of clamp 500.

The body 502 and each of the rack housing 510 and pawl housing 550, which inter-fit to form two-piece body 502, are cylindrical or substantially cylindrical in shape with rod-shaped jaws 540, 584 extending therefrom.

Clamp 500 further comprises a bias 594 which in the embodiment shown comprises an open-cell foam 596. Although FIG. 5H shows only a single bias 594 to be housed in rack housing 510, in other embodiments both rack housing 510 and pawl housing 550 house a bias 594. From the teaching herein, a skilled person is readily able to select another mechanical device to generate the opening force such as, a spring including a coiled spring. The bias 594 may be selected to produce a minimum force for opening.

Bias 594 rests on top of plunger 566 which comprises a cup 568 and a stem 570. The cup 568 supports the bias 594 so that when the pair of jaws 506 close, bias 594 is compressed. When a bias 594 is present in both rack housing 510 and pawl housing 550, the bias may have a channel for accommodating the stem 570 and the cup 568 may slide up and down the stem 570.

Clamp 500 provides graduated movement and/or clamping force and clamping distance by using actuator 578 and/or bases 512 and 554 to select a desired one of rack ridges 526a-f. To release clamp 500, actuator 578 may be utilised by squeezing flanges 580 which buckles pawl housing 550 inwards at the button sides and outwards at the racks 524 to disengage rack teeth 576a,b from rack ridges 526a-f so that bias 594 pushes the pair of jaws 506 apart to disengage clamping.

The cushioning by pads 546 is at least in part provided by fluid 507 (not shown) disposed in fluid line 508 which is comprised of rack housing reservoir 528; pawl housing reservoir 562; rack jaw reservoir 549; pawl jaw reservoir 593; rack passage 530; and pawl passage 574. Rack passage 530 joins rack housing reservoir 528 and rack jaw reservoir 549. Pawl passage 574 joins pawl housing reservoir 562 and pawl jaw reservoir 593.

Fluid line 508 is also shown to comprise channel 509, see FIG. 5G. Channel 509 comprises the part of fluid line 508 which joins rack housing 510 and pawl housing 550. In the embodiment shown in FIG. 5G, pawl channel 571 is shown running through both cup 568 and stem 570 of plunger 566 in pawl housing 550. The absence of a plunger in rack housing 510 means a rack channel 532 (not shown) is not required in this embodiment. Channel 509 then comprises those of rack channel 532 (not shown) and pawl channel 571 required for an open system.

Fluid line 508 comprises an open system so that equal pressure is applied to both pads 546,590. Closing the pair of jaws 506 increases the amount of fluid 507 or and/or pressure of the fluid 507 in the pair of jaws 506 and the membranes 548,592 and/or pads 546,590 expand to contain the pressurised fluid 507. When the fluid 507 is comprised in an open system, both jaws 540,584 are connected to maintain the fluid pressure equal across both membranes 548,592 and/or pads 546,590. Opening the pair of jaws 506 releases the fluid pressure and contracts the membranes 548,592 and/or pads 546,509.

Fluid 507 may be any suitable gas, liquid or gel such as, air or saline. The fluid may be a compressible or incompressible fluid. The open cell foam 596 is filled or partly filled with fluid 507.

In the embodiment shown, fluid 507 is impelled by the mechanical device 504. The force associated with the impelling is generated by the opening and closing of the pair of jaws 506. Opening pair of jaws 506 decreases the amount of fluid 507 in one or both of the rack jaw reservoir 549 and the pawl jaw reservoir 593 and proportionately increases the amount of fluid 507 in one or both of the rack housing reservoir 528 and the pawl housing reservoir 562. Closing the pair of jaws 506 increases the amount of fluid 507 in one or both of the rack jaw reservoir 549 and the pawl jaw reservoir 593 and proportionately decreases the amount of fluid 507 in one or both of the rack housing reservoir 528 and the pawl housing reservoir 562. The increase and decrease in the amount of fluid 507 in the rack jaw reservoir 549 and the pawl jaw reservoir 593 inflates and deflates membranes 548, 592.

In another embodiment, the proportionate increase in the amount of fluid 507 in one or both of the rack jaw reservoir 549 and the pawl jaw reservoir 593 on closing of the pair of jaws 506 and proportionate decrease in the amount of fluid 507 in one or both of the rack jaw reservoir 549 and the pawl jaw reservoir 593 on opening of the pair of jaws 506 is independent of the movement of the pair of jaws 506.

The differential cushioning provided by increasing and decreasing the amount of fluid 507 in the rack jaw reservoir 549 and the pawl jaw reservoir 593 provides the user with greater control of the degree of force being applied to the blood vessel, tissue or other body part and a gentler and/or softer surface with improved probability of conforming to the blood vessel, tissue or other body part to thereby reduce the likelihood of trauma or damage.

The compression of the one or more bias 594 may result in proportionate closing of the pair of jaws 506. The decompression of the one or more bias 594 may result in proportionate opening of the pair of jaws 506.

In use, the entire surgical clamp 500 remains inside the subject. To reduce or to minimise the likelihood of trauma, one or more or each exposed surface of clamp 500 may comprise a bevel or other safety feature.

From the above description it is clear that surgical clamp 500 is a mechanical clamp and does not comprise any electronic or electromechanical components.

Clamp 500 may be used to clamp a blood vessel, tissue or other body part. In a particular embodiment, surgical 500 clamp is a haemostatic clamp but is not so limited.

The invention also provides a method of manufacturing clamp 500. Clamp 500 may be comprised of any suitable surgical grade material such as, but not limited to, one or more of silicone, a polymer or a metal.

Although not shown, surgical clamp 500 may comprise a visibility or locatory feature such as a high-vis colour.

The surgical clamp 500 may be used in laparoscopic or keyhole surgery.

From the teaching herein, a skilled person understands that surgical clamp 500 may be used with any suitable animal. While not limited thereto, the animal may be a mammal and the mammal may be a human. Surgical clamp 500 may also be used with a companion animal such as, a canine or a feline, livestock such as, an equine, a bovine, an ovine, a porcine, a hircine.

Advantageously, clamp 500 provides graduated clamping and thereby provides more control over the clamping force applied. This has the advantage of reducing the likelihood of damage to the blood vessels and reducing the likelihood of plaque dislodgement.

Conventional surgical clamps have been shown to cause damage to the internal endothelial layer of blood vessels. Advantageously, the present invention provides graduated clamping which reduces the likelihood of this type of damage. On the other hand, conventional spring loaded clamps may apply insufficient force to interrupt blood flow.

Clamp 500 allows the user to determine the level of clamping force to accomplish sufficient clamping without damage.

Advantageously, the present invention provides graduated clamping and gives the health care professional control over the force applied to effect the clamping. This is in stark contrast to prior art clamps that do not give the health care professional any control over clamping. With conventional "all or nothing" clamps, the user must apply the closing force that is predetermined by the clamping mechanism provided in the clamp. With other prior art devices that clamp via elongate shafts or handles, it is difficult to estimate or adjust the clamping force because the actuator is distal from the site of clamping and a large amount of leverage may be utilised.

In this specification, the terms "comprises", "comprising" or similar terms are intended to mean a non-exclusive inclusion, such that an apparatus that comprises a list of elements does not include those elements solely, but may well include other elements not listed.

Throughout the specification the aim has been to describe the invention without limiting the invention to any one embodiment or specific collection of features. Persons skilled in the relevant art may realize variations from the specific embodiments that will nonetheless fall within the scope of the invention.

The invention claimed is:

1. A surgical clamp comprising:
  a two-piece body comprising a top jaw housing that inter-fits with a bottom jaw housing;
  the top jaw housing comprising a top jaw and a top wall, the top wall comprising an open slot through which a lever extends to contact a rack;
  the bottom jaw housing comprising a bottom jaw, a bottom wall, and a bottom base, the bottom base comprising a shoulder;
  the inter-fitting top jaw housing and bottom jaw housing disposed for movement relative to one another, the top wall and the bottom wall moving along each other's length in a telescopic movement delimited by a top wall upper surface abutting the shoulder;
  a bias to separate the top jaw housing and bottom jaw housing apart and to urge the top jaw and the bottom jaw apart; and
  the lever moveable between a lock position and an open position and the lever disposed to prevent opening movement of the top jaw housing relative to the bottom jaw housing and to allow graduated relative closing movement of the top jaw housing relative to the bottom jaw housing in the lock position and to allow opening and closing movement of the top jaw housing relative to the bottom jaw housing in the open position;
  wherein the lever comprises an axial arm and a lateral arm, the axial arm extending in a direction between the top jaw housing and the bottom jaw housing, the lateral arm extending in a direction of the top jaw and the bottom jaw, wherein the axial arm comprises one or more tooth or pawl disposed at a distal end of the axial arm and the lateral arm comprises a button disposed on a distal end of the lateral arm, wherein the one or more tooth or pawl is disposed on a jaw side of the surgical clamp to extend through the open slot to thereby contact the rack and the button is disposed on an opposite side of the surgical clamp;
  wherein the lever comprises an integral component comprising the lateral arm and the axial arm and the button in one piece, wherein pressing the button or the distal end of the lateral arm obliquely pivots or moves the axial arm out of the open slot and disengages the one or more tooth or pawl from the rack;
  wherein the button comprises a region of the lever of increased width to assist in applying a force required to pivot or move the lever; and
  wherein the lever comprises a top bias retaining surface and the bottom jaw housing comprises a bottom bias retaining surface to retain the bias therebetween;
  such that compressive force applied to one or more of the top jaw housing and the bottom jaw housing causes graduated closing movement of the top jaw housing and the bottom jaw housing to close the top jaw and the bottom jaw.

2. The surgical clamp of claim 1, wherein the top jaw housing comprises a push tab.

3. The surgical clamp of claim 1, wherein the top wall and/or bottom wall define an internal cavity or void.

4. The surgical clamp of claim 1, wherein a force applied by the bias is selectable.

5. The surgical clamp of claim 1, wherein the bias comprises a pre-set clamping force.

6. The surgical clamp of claim 1, wherein each jaw further comprises a cushion and moving the top jaw and bottom jaw relative to each other to open and close the top jaw and bottom jaw increases or decreases fluid in one or both cushions.

7. The surgical clamp of claim 6, wherein a force associated with impelling the fluid is generated by opening and closing the top jaw and bottom jaw.

8. The surgical clamp of claim 6, further comprising a fluid line.

9. A method of clamping a blood vessel, tissue or other body part with the clamp of claim 1.

10. A method of manufacturing a surgical clamp, the method comprising:
  assembling a two-piece body comprising a top jaw housing that inter-fits with a bottom jaw housing, a bias to separate the top jaw housing and bottom jaw housing apart and to urge a top jaw and a bottom jaw apart, and a lever, the lever moveable between a lock position and an open position and the lever disposed to prevent opening movement of the top jaw housing relative to the bottom jaw housing and to allow graduated relative closing movement of the top jaw housing relative to the bottom jaw housing in the lock position and to allow opening and closing movement of the top jaw housing relative to the bottom jaw housing in the open position;
  the top jaw housing comprising the top jaw and a top wall, the top wall comprising an open slot through which the lever extends to contact a rack;
  the bottom jaw housing comprising the bottom jaw, a bottom wall, and a bottom base, the bottom base comprising a shoulder; and
  the inter-fitting top jaw housing and bottom jaw housing disposed for movement relative to one another, the top wall and bottom wall moving along each other's length in a telescopic movement delimited by a top wall upper surface abutting the shoulder;
  wherein the lever comprises an axial arm and a lateral arm, the axial arm extending in a direction between the top jaw housing and the bottom jaw housing, the lateral arm extending in a direction of the top jaw and the bottom jaw, wherein the axial arm comprises one or more tooth or pawl disposed at a distal end of the axial arm and the lateral arm comprises a button disposed on a distal end of the lateral arm, wherein the one or more tooth or pawl is disposed on a jaw side of the surgical clamp to extend through the open slot to thereby contact the rack and the button is disposed on an opposite side of the surgical clamp;

wherein the lever comprises an integral component comprising the lateral arm and axial arm and the button in one piece, wherein pressing the button or the distal end of the lateral arm obliquely pivots or moves the axial arm out of the open slot and disengages the one or more tooth or pawl from the rack;

wherein the button comprises a region of the lever of increased width to assist in applying a force required to pivot or move the lever; and wherein the lever comprises a top bias retaining surface and the bottom jaw housing comprises a bottom bias retaining surface to retain the bias therebetween;

such that compressive force applied to one or more of the top jaw housing and the bottom jaw housing causes graduated closing movement of the top jaw housing and the bottom jaw housing to close the top jaw and the bottom jaw.

11. The method of claim 10, wherein a force applied by the bias is selectable.

12. The method of claim 10, wherein the bias comprises a pre-set clamping force.

13. The method of claim 10, wherein each jaw further comprises a cushion and moving the top jaw and bottom jaw relative to each other to open and close the top jaw and the bottom jaw increases or decreases fluid in one or both cushions.

14. The method of claim 13, wherein a force associated with impelling the fluid is generated by opening and closing the top jaw and the bottom jaw.

* * * * *